United States Patent
Xu et al.

(10) Patent No.: US 11,279,916 B2
(45) Date of Patent: Mar. 22, 2022

(54) ENZYME AND APPLICATION THEREOF

(71) Applicant: SHANGHAI JIAO TONG UNIVERSITY, Shanghai (CN)

(72) Inventors: Ping Xu, Shanghai (CN); Hongzhi Tang, Shanghai (CN); Kunzhi Zhang, Shanghai (CN); Geng Wu, Shanghai (CN); Fei Tao, Shanghai (CN)

(73) Assignee: Shanghai Jiao Tong University, Shanghai (CN)

( * ) Notice: Subject to any disclaimer, the term of this patent is extended or adjusted under 35 U.S.C. 154(b) by 180 days.

(21) Appl. No.: 16/090,535

(22) PCT Filed: Mar. 31, 2017

(86) PCT No.: PCT/CN2017/078912
§ 371 (c)(1),
(2) Date: Feb. 7, 2019

(87) PCT Pub. No.: WO2017/167250
PCT Pub. Date: Oct. 5, 2017

(65) Prior Publication Data
US 2019/0153403 A1    May 23, 2019

(30) Foreign Application Priority Data
Apr. 1, 2016  (CN) .......................... 201610205619.5

(51) Int. Cl.
*C12N 9/06* (2006.01)
*A61K 38/44* (2006.01)
*A61P 25/34* (2006.01)

(52) U.S. Cl.
CPC ............ *C12N 9/0012* (2013.01); *A61K 38/44* (2013.01); *A61P 25/34* (2018.01); *C12Y 105/99004* (2013.01)

(58) Field of Classification Search
None
See application file for complete search history.

(56) References Cited

U.S. PATENT DOCUMENTS
2016/0032298 A1    2/2016   Hashimoto et al.

FOREIGN PATENT DOCUMENTS
CN  102796681 A  11/2012
CN  103952429 A   7/2014
WO  WO 2017/023904 A3 *  9/2017  ......... A61K 31/4439

OTHER PUBLICATIONS

Genebank : CP006979.1, Pseudomonas monteilii SB3101, complete genome, Jun. 18, 2014. Downloaded PDF p. 1 of 120 on May 11, 2020. (Year: 2014).*
Pseudomonas monteilii SB3101, complete genome, p. 1 from Genebank CP006979.1, Jun. 18, 2014 (downloaded Sep. 14, 2020) (Year: 2014).*
Tararina, M. et al., "Structural Analysis Provides Mechanistic Insight into Nicotine Oxidoreductase from Pseudomonas putida", Biochemistry 55(48): 6595-6598 (Year: 2016).*
Patent Cooperation Treaty, International Search Report of the State Intellectual Property Office of the Peoples Republic of China for International Application No. PCT/CN2017/078912 dated Jul. 11, 2017 and English Translation, 12 pages.
Patent Cooperation Treaty, Written Opinion of the International Searching Authority for International Application No. PCT/CN2017/078912 dated Nov. 7, 2017 and English Translation, 10 pages.

* cited by examiner

*Primary Examiner* — Anand U Desai
(74) *Attorney, Agent, or Firm* — Fitch, Even, Tabin & Flannery, LLP

(57) ABSTRACT

Provides an artificial enzyme obtained by improving upon a sequence of a natural nicotine dehydrogenase, wherein the improvement comprises replacing at least one amino acid hindering product release with an amino acid with smaller side chains, thereby improving a catalytic rate.

1 Claim, 4 Drawing Sheets

Specification includes a Sequence Listing.

```
                       160        170        180        190        200        210        220        230        240        250        260
                        |          |          |          |          |          |          |          |          |          |          |
                        →                                                                                          →→        →→→
158 NIKIAFEKLCHDAWEVFPRPH-EPMFTERA-RELIDKSSVLDRIKTLGLSRLQQAQINSTMALYAGETTDKFGLPGVLKLFACCGWNVDAFMDTET--HYRIQGGTIGLLNA 264  NicA2     SEQ ID NO: 1
111 VEAATYTLLRDAHRIDLEKGLEN-----QDLEDID-IPINEYVDKLIDLPPVSRQFLLAWAWNMLGQPADQASALWMLQLVAANHYSILGVLSLD--EV-FSNGSADLVDA 212  6HLNO     SEQ ID NO: 12
154 NIQVAFERMCHDAWEAFPRPH-EPMFTERA-RKLIDRMSVLDRINQLRLTRAQRAELNSYMALYGGETTDKYGLPGVLKLFACCGWNVAFMDTET--HYRIEGGTIGLLNA 260  NOX       SEQ ID NO: 13
158 LYE-ALDAFYVEARQVWDRPY-DAQYTWNELIRRDKRTGQQRLDELKLNPVQRVAIDSFVGATAHAPLDQTSYVDMLRYWALSGWNLQGFNDAVV--RYKLKDGTVGLINK 264  Pa WP_042909960.1 SEQ ID NO: 14
113 AIESLMEMVVQDAREVLEREF-EPFFHKDALEVIDKLSIQDRIDGLDLITPEEKDLANGLWTAMSAPCGDVGLVAALRWYALSGFDINAVFDTVG--RYKLKNGTRSLIQA 220  Rw WP_037238225.1 SEQ ID NO: 15
103 RVRELFTRFAGDAGALLPHPH-DPL-RVTGVAALDARSMQDRLDEMRLTGSDEEMLSGLLIYEIAGSPLDEAALLQVVRWMALSDWDIDRWYIDN--RYRPVGGTVAVLDG 208  Cw WP_041732229.1 SEQ ID NO: 16
152 LLEDALKRFHAEAGEVFERRF-MAGLSAAG-RKLDHLSIADRMAAMEMSPAQRDLMNAMMATNCHGPIATGAYTEMLRWMSLVDGDAARLLYSCA--RYKLKDGTAALIER 258  Tp WP_004360663.1 SEQ ID NO: 17
110 LIERGMDRIAEDSREFFEMPY-EPLRHRG-LDAIDHESVVDYFGRLDLDPTEREVTTGVWAEHFNAPAEVSGLAQAMRWCAAASGDWRLLHEATS--GYRLGTGTAAIASA 216  Se WP_009946785.1 SEQ ID NO: 18
123 DLSAALQLFCDVDGARGEIAFANPHCPDPVADRFDSISLAERLAQIELSSRQRALLEAFVTMNAATDPAKGGFYDQLRWWALGEYSTEALLKRLG--RYKIAKGTSALAIA 231  Hs WP_041311591.1 SEQ ID NO: 19
119 IAYLDYNNLWRTIDNMGKEIPTDAPWEAQAHADKWDRMTMKELIDKICWTKTARRFAYLFVNINVTSEPHEVSALWLMWLVKQCGGTTRIFSVTNGGQERKFVGGSGQVSER 229  human MAO-A SEQ ID NO: 20
110 ITYLDHNNFWRTMDDMGREIPSDAPWKAPLAEEWDNMTMKELLIDKLCWTESAKQLATLFVNLCVTAETHEVSALWLMWLVKQCGGTTRIISTTNGGQERKFVGGSGQVSER 220  human MAO-B SEQ ID NO: 21

270        280        290        300        310        320        330        340        350        360
                        |          |          |          |          |          |          |          |          |          |
                                                                                                      →          →
265 MLTDSGAEVRMSVPVTAVEQVNGGVKIKTDDEIITAGVVVMTVPLNTVKHIGFTPALSKGKQRFTKEG--QLSKGAKLYVHVKQNLGRV---F-----AFADEQPLNWVQTH 368  NicA2     SEQ ID NO: 1
213 M-SQEIPEIRLQTVVTGIDQSGDVVNVTVKDCHAFQAHSVIVATPANTWRRIVFTPALPERRRSVIEEG-HGGQGLKILIHVRGA---EAGI--ECVGDGIFPTLYDYCE 315  6HLNO     SEQ ID NO: 12
261 MLADSGAEVRLNMPVISVEQLNGGVRVETDDGETIIAGTIIMTVPLNTVRHINFTPALSEGKQRFIQEG--QLSKGAKLYVHVKENLGRV---F-----AFADEQPLNWVQTH 364  NOX       SEQ ID NO: 13
266 MIEDGKPQVRLSTPVKKIEDKGDHTVVTTQKGEKIVAASVIIALPMNVLPNLEFSPALDPVLIEAGKQK-HSGKGINFYIKARGGFTKLAKV---TAMADSNYPVNLVMAH 371  Pa WP_042909960.1 SEQ ID NO: 14
221 IADDSSAEIRLSTPVAAVEQSDDGVVVTTRQGDTLRARYVVVAAPLNTFGAIDESPPLSAAKQAGISEG--QPGRGSKAWVHVRGDLPKP--F-----FAVAPENHLINYVVTD 325  Rw WP_037238225.1 SEQ ID NO: 15
209 IVASGRFDVQLSAPVSAVDAGRDAVRVVTRDGRAFRASTVVIATPVNVWPHIDFGPGLPAAHREAGRVGWGKPBQDKVWIEVRGSLGRV---F-----GQLPAPAPLNFFWTHE 314  Cw WP_041732229.1 SEQ ID NO: 16
259 MAEDGGFDVRLSTAVAELSQDAAGVSLVTEADERISARYAVVAVVPVNTAGQIEFSPPLRPGKTAWAKEH-HAGKGHKLYLKVKGRLETL---I----F-FAPETELFTMVFTD 362  Tp WP_004360663.1 SEQ ID NO: 17
217 MAEDGDAEFLRTVTAVRQEDGRATATTADGKRYTARRIVCTLPLNVLGSIDFQPGLPAAKLAASAER-TASQGLKTWIRVGHIA-P---F-----TAYAPDDHALTFVRPE 320  Se WP_009946785.1 SEQ ID NO: 18
232 LLKDSKADLFVGEPVSEITARADGVALQARNI-SLQAKSLVVAVPMNVLGDIRFTSGLPQAREQ-AHRQRHVCAGTKFIAQVDRNVG----AW-----IGFAPYPNALTMVISD 334  Hs WP_041311591.1 SEQ ID NO: 19
230 IMDLLGDQVKLNHPVTHVDQSSDNIIIETLNHEHYECKYVINAIPPTLTAKIHFRPELPAERNQLIQR-LPMGAVIKCMVYKEAFWKKDYCGCMIIEDEDAPISIILDD 332  human MAO-A SEQ ID NO: 20
221 IMDLLGDRVKLERPVTYIDQTRENVLVETLNHEMYRAKYVISAIPPTLGMKIHFNPPLPMRNQMITR-VPLGSVIKCIVYKEPFWRKKDYCGTMIDGEEAVYTLDD 330  human MAO-B SEQ ID NO: 21
```

Fig. 11

ENZYME AND APPLICATION THEREOF

CROSS-REFERENCE TO RELATED APPLICATIONS

This application is a U.S. national phase application filed under 35 U.S.C. § 371 of International Application Number PCT/CN2015/078912, filed Mar. 31, 2017, designating the United States, which claims priority from Chinese Patent Application Number CN 201610205619.5, filed Apr. 1, 2016.

REFERENCE TO A SEQUENCE LISTING

The Sequence Listing associated with this application is filed in electronic format via EFS-Web and is hereby incorporated into the specification in its entirety. The name of the text file containing the Sequence Listing is "Sequence_Listing." The size of the text file is 12.2 KB, and the text file was created on Nov. 13, 2018.

FIELD OF THE INVENTION

The present invention belongs to the field of protein engineering and relates to a protein mutant, in particular to a nicotine dehydrogenase mutant and application thereof in areas such as for developing protein drug for treating nicotine addiction.

DESCRIPTION OF THE PRIOR ART

Nicotine (1-methyl-2-[3-pyridine]-pyrrolidine) is one of main harmful ingredients in tobacco leaves, cigarette smoke and tobacco waste, which is harmful to human health and is an important precursor of nitrosamine (TSNA) that is the main carcinogenic ingredient in tobacco. In China, a great amount of tobacco with a high nicotine content is produced in the tobacco production each year, which not only affects smoking quality of tobacco seriously, but also increases harmfulness of tobacco.

Therefore, reducing the contents of nicotine in tobacco and environment is of extremely important significance to maintain human health and to protect ecological environment.

The degradation of nicotine by microorganisms is a new approach to reduce contents of nicotine in tobacco and environment and nicotine's harmfulness, especially *Pseudomonas* and *Arthrobacter* can metabolize and decompose nicotine to generate the essential carbon source, nitrogen source and energy for their growth. Bacteria which have been discovered to be able to metabolize nicotine include *Pseudomonas* (for example, *Pseudomonas* sp. No. 41, *P. convexa* PC1, *P. putida*), *Arthobacter* (for example, *Arthrobacter oxidans* P-34, which was re-identified as *A. ureafaciens; A. oxidans* pAO1 later, and then was re-identified as *Arthrobacter nicotinoborans* later), *Cellulomonas* sp., and *Ochrobactrum intermedium*. The fungi mainly include *Cunninghamella echinulata, Microsporum gypseum, Streptomyces griseus, S. platenses* and *Pellicularia filamentosa*.

It has been found that microbial metabolism of nicotine is mainly through three pathways: Pyridine pathway (mainly in *Arthrobacter* sp), Pyrrolidine pathway (mainly in *Pseudomonas* sp.) and Me pathway (mainly existing in the fungi). In the Pyrrolidine pathway, the pyrrole ring of nicotine is oxidized to produce methylmyosmine, and when water is added, ring opening of methylmesamine occurs to form pseudooxynicotine, which is further demethylated to form 3-carboxylic acid pyridinium salt, and the 6' position of the pyridine ring is re-hydroxylated to form a 6-hydroxy, 3-carboxylic acid pyridinium salt, and after side chain is removed, 2, 5-dihydroxy-pyridinium salt and succinate salt are formed. This metabolic pathway can also start with 6-hydroxy pseudooxynicotine, and eventually 2, 5-dihydroxy-pyridinium salt and succinate salt are produced.

The nicotine dehydrogenase NicA2 is an enzyme recently isolated from *Pseudomonas putida* S16 that can degrade nicotine. The reports related to nicotine dehydrogenase NicA2 can be found in: *PLoS Genet.* 2013 October; 9(10): e1003923. doi: 10.1371/journal.pgen. 1003923. Epub 2013 Oct. 24. Systematic unraveling of the unsolved pathway of nicotine degradation in *Pseudomonas*. Tang H, Wang L, Wang W, Yu H, Zhang K, Yao Y, Xu P.

In the first step of dehydrogenation reaction of nicotine degradation catalyzed by Nicotine dehydrogenase NicA2, nicotine (I) is converted to N-methymyosmine (II), which can further be subjected to a spontaneous hydration reaction to produce pseudooxynicotine (III).

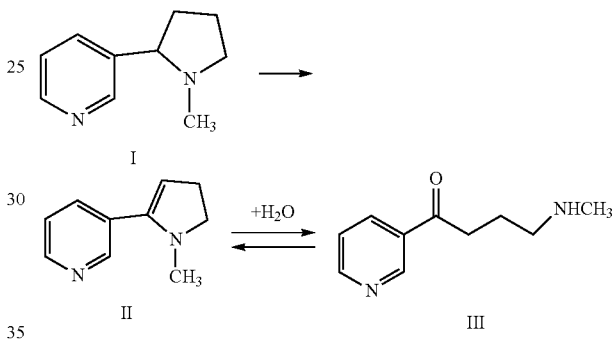

NicA2 is encoded by nicA2 gene, and plays a crucial role in the degradation pathway of nicotine metabolized by *Pseudomonas putida* S16. When the nicA2 gene is knocked out, *Pseudomonas putida* S16 cannot grow with nicotine as the sole carbon and nitrogen source (*PLoS Genet.* 10.1371/journal.pgen. 1003923).

NicA2 belongs to the family of monoamine oxidase (MAO). MAO mainly exists on the outer membrane of mitochondria and its main role in the organism is to catalyze the metabolism of endogenous and exogenous monoamines. Under the action of MAO, monoamines are oxidized to generate deamination. MAO can be divided into two categories, i.e., MAO-A and MAO-B, according to substrates, distribution locations, and selective inhibitors for MAO. MAO-A has high affinity for serotonin (5-HT), norepinephrine (NE) and dopamine (DA) (*J. Mol. Biol* 338, 103-114); and MAO-B has high affinity for phenethyl amines (PEA) and benzylamine, etc. (*Proc. Natl Acad. Sci. USA* 100, 9750-9575).

In the initiation of nicotine degradation by *Pseudomonas putida*, NicA2 catalyzes nicotine to produce pseudooxynicotine, providing the initial impetus for the entire metabolic pathway. Research on the nicotine metabolic pathway by Xu Ping's Research Group has confirmed that subsequent 6-hydroxy-3-succinylpyridine monooxygenase (HspB) and 2,5-dihydroxypyridine dioxygenase (HPO) can further catalyze deacidification and ring opening of nicotine, to form a simple structure, which finally enters the tricarboxylic acid cycle (*J. Biol. Chem.* 42: 29158-29170; *Sci. Rep./*3-3235/DOI:10.1038/srep03235). Therefore, the first step of processing of nicotine by NicA2 initiates efficient operation of the subsequent enzyme catalysis and even the entire metabolic pathway. The catalytic efficiency of NicA2 is the key point for determining the whole metabolic efficiency for nicotine and is a key factor for the construction of subsequent metabolic pathways. The article "A new strategy for smoking cessation: characterization of a bacterial enzyme for the degradation of nicotine" published in *JACS* in 2015 initially reported the possibility of NicA2 for treating cigarette addiction. The report points out that NicA2 has high efficiency and stability for the catalysis of substrate nicotine, and even in the mouse serum, NicA2 can maintain a high activity at 37° C. In addition, NicA2 has high affinity for the substrate nicotine, which catalyzes the degradation of nicotine with a $K_m$ value of 91.9 nM, while the highest nicotine content in blood is between 162 and 370 nM. So, theoretically, if NicA2 can successfully function in degradation of nicotine in human body, then the nicotine content in the human body is in a saturated level for NicA2. The key for developing protein drugs with nicotine dehydrogenase is the high-efficiency nicotine dehydrogenase. The higher the activity of the enzyme is, the lower the amount of developed drug is and the better the effect is. The wild type enzyme has limitation in a catalytic rate. If the enzyme can be modified by a protein engineering method to increase its catalytic efficiency, the development and utilization of nicotine dehydrogenase can be greatly facilitated.

Therefore, those skilled in the art are directed to developing a nicotine dehydrogenase with a high catalytic rate and its application in the biocatalysis, metabolic engineering modifications, and protein drug development.

SUMMARY OF THE INVENTION

In view of the foregoing drawbacks of the prior art, the technical problem to be solved by the present invention is to modify a nicotine dehydrogenase to obtain a nicotine dehydrogenase with a high catalytic rate and application thereof.

In order to achieve the above objects, in one aspect, the present invention provides an artificial enzyme.

In one particular embodiment of the present invention, the artificial enzyme is manufactured by modifying a sequence of a natural enzyme, wherein the natural enzyme has the activity for catalyzing the conversion reaction from compound I to compound II, as shown by the following formula,

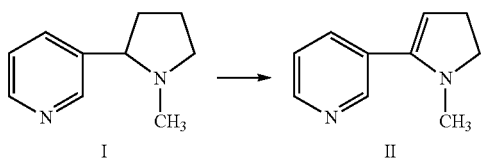

or, the natural enzyme is nicotine dehydrogenase;
wherein the modification comprises: substituting at least one of the amino acids that block product release with amino acids with smaller side chains.

Further, the natural enzyme has one or more of the following features:
1) the amino acid sequence of the natural enzyme includes amino acid sequence with more than 85%, or more than 90%, or more than 95%, or more than 98%, or more than 99% homology to the amino acid sequence shown in SEQ ID NO: 1; or the amino acid sequence of the natural enzyme includes the amino acid sequence shown in SEQ ID NO:1; or the amino acid sequence of the natural enzyme is as shown in SEQ ID NO:1;

2) the natural enzyme is encoded by nucleic acid hybridized with complementary chain of nucleic acid encoding protein with an amino acid sequence shown by SEQ ID NO:1 under a high stringent condition; and
3) the natural enzyme exists in the microorganism *Pseudomonas*.

Further, the natural enzyme exists in *Pseudomonas putida* S16.

Further, the natural enzyme has a product release channel for product release, the amino acid whose side chains are located in the product release channel of the natural enzyme includes at least one of tryptophan, tyrosine, phenylalanine, glutamic acid and methionine; and the above modification comprises: substituting at least one of the tryptophan, tyrosine, phenylalanine, glutamic acid and methionine whose side chains are located in product release channel of natural enzyme with amino acids with smaller side chains.

Further, there are at least 9 amino acids whose side chains are located in product release channel of the natural enzyme, and the 9 amino acids are selected from tryptophan, tyrosine, phenylalanine, glutamic acid and methionine.

Further, the three-dimensional structure of the natural enzyme at least comprises one β-sheet and one α-helix located at the release channel, 3 of the 9 amino acids are located at the β-sheet, according to the relative positions, the 3 amino acids are phenylalanine at position 353, phenylalanine at position 355 and tryptophan at position 364 respectively; 6 of the 9 amino acids are located at α-helix, according to the relative positions, the 6 amino acids are the phenylalanine at position 163, tyrosine at position 214, tyrosine at position 218, tyrosine at position 242, methionine at position 246 and glutamic acid at position 149, respectively.

Further, the substituting modes are: if the amino acid to be substituted is located on β-sheet, the amino acid is substituted with valine; if the amino acid to be substituted is located on α-helix, the amino acid is substituted with alanine.

Preferably, the modification comprises: substituting all amino acids that block product release and have a molecular weight of more than 120 with amino acids with smaller side chains.

In another aspect, the present invention provides an enzyme, and in one particular embodiment, the enzyme has one or more of the following features:
1) the amino acid sequence of the enzyme includes amino acid sequence with more than 85%, or more than 90%, or more than 95%, or more than 98%, or more than 99% homology to the amino acid sequence shown in SEQ ID NO: 2; or the amino acid sequence of the enzyme includes the amino acid sequence shown in SEQ ID NO: 2; or the amino acid sequence of the enzyme is as shown in SEQ ID NO: 2;
2) the enzyme is encoded by nucleic acid hybridized with complementary chain of nucleic acid encoding protein with an amino acid sequence shown by SEQ ID NO: 2 under a high stringent condition; and
3) the amino acid sequence of the enzyme includes the amino acid sequence in which the amino acid sequence as shown in SEQ ID NO: 2 is conservatively substituted; wherein, according to the relative positions, at least one of the amino acids at positions 353, 355 and 364 of the enzyme is a first small-molecular-weight amino acid; at least one of the amino acids at positions 163, 214, 218, 242, 246 and 249 of the enzyme is a second small-molecular-weight amino acid, and the first small-molecular-weight amino acid has a molecular weight less than 140, and the second small-molecular-weight amino acid has a molecular weight less than 110.

Further, the enzyme has the activity for catalyzing the conversion reaction from compound I to compound II as shown by the following formula:

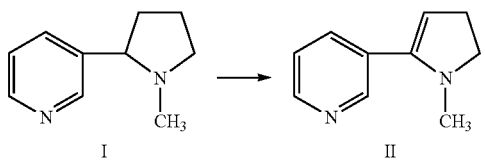

or, the enzyme is nicotine dehydrogenase.

Further, the amino acids at positions 353, 355 and 364 are located in β-sheet; and the amino acids at positions 163, 214, 218, 242, 246 and 249 are located in α-helix.

Further, the first small-molecular-weight amino acid is valine, and the second small-molecular-weight amino acid is alanine.

Preferably, the amino acids at positions 353, 355 and 364 are all first small-molecular-weight amino acids, and the amino acids at positions 163, 214, 218, 242, 246 and 249 are all second small-molecular-weight amino acids.

In still another aspect, the present invention provides an enzyme, and in one particular embodiment, the enzyme has the activity for catalyzing the conversion reaction from compound I to compound II as shown by the following formula:

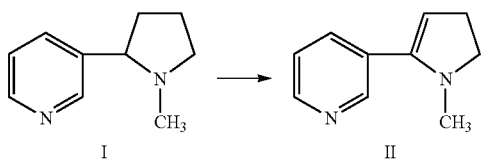

or, the enzyme is nicotine dehydrogenase.

The enzyme has a product release channel for product release, and the amino acid with side chains located at the narrowest site of the product release channel has a molecular weight of less than 140.

Preferably, the amino acid with side chains located at the narrowest site of the product release channel has a molecular weight of less than 120.

Preferably, the amino acid with side chains located at the narrowest site of the product release channel is valine or alanine.

In another aspect, the present invention provides a nucleotide sequence that encodes the artificial enzyme or enzyme.

Further, the nucleotide sequence has one or more of the following features:
1) the nucleotide sequence includes the nucleotide sequence with more than 85%, or more than 90%, or more than 95%, or more than 98%, or more than 99% homology to the nucleotide sequence shown in SEQ ID NO:3; or the nucleotide sequence includes the nucleotide sequence shown in SEQ ID NO:3; or the nucleotide sequence is as shown in SEQ ID NO:3; and
2) the nucleotide sequence can be hybridized with complementary chain of nucleotide sequence shown by SEQ ID NO:3 under a high stringent condition.

In still another aspect, the present invention provides an expression vector or a host cell containing the above nucleotide sequence.

In still another aspect, the present invention provides application of the above artificial enzyme or the enzyme in degradation of nicotine.

The present invention further provides application of the above artificial enzyme or the enzyme in preparation of drugs for treating nicotine addiction.

The present invention further provides use of the above artificial enzyme or the enzyme in preparation of enzyme preparations for biocatalytic conversion.

The present invention further provides application of the above artificial enzyme or the enzyme in metabolic engineering modifications and synthetic biology.

In still another aspect, the present invention provides a method for modifying enzymes of monoamine oxidase family, wherein the method comprises: substituting at least one of the amino acids that block product release with amino acids with smaller side chains.

In the present invention, the crystal structure analysis is performed by protein engineering methods starting from wild-type nicotine dehydrogenase, to obtain the relevant structure that affects product release, and influence of related amino acids on the product release is eliminated by means of amino acid substitution, thereby improving the catalytic rate of mutant enzyme. In a preferred embodiment of the invention, although the affinity of the nicotine dehydrogenase mutant is slightly weaker than that of the wild-type nicotine dehydrogenase, the nicotine dehydrogenase mutant's rate for catalyzing the substrate nicotine is much higher than that of wild-type nicotine dehydrogenase, that is, 3.67 times.

The present invention firstly analyzes the structure of nicotine dehydrogenase and obtains a binding structure of nicotine dehydrogenase and substrate nicotine. 9 large amino acid residues hindering product release are obtained through analysis on the foregoing structure and related experiments, which lays a solid foundation for the subsequent mutation to obtain nicotine dehydrogenase with high catalytic efficiency.

In addition, the foregoing 9 large amino acid residues that hinder product release have certain conservation among other members of the monoamine oxidase family, laying a good basis for modifying members of the monoamine oxidase family.

The nicotine dehydrogenase mutant of the present invention can be applied at least in biocatalysis, metabolic engineering and synthetic biology as well as development of protein drugs, with promising commercial application prospects:
(a) biocatalysis: the nicotine dehydrogenase mutant obtained in the present invention has superior catalytic properties than natural nicotine dehydrogenase, which can be used to acquire higher catalytic properties for catalyzing nicotine into a product, and thus, it can be used for development of enzyme preparations for biocatalysis conversion;
(b) metabolic engineering and synthetic biology: the above obtained mutant can perform the same catalytic reactions as the natural nicotine dehydrogenase, but it has higher catalytic efficiency, thus it can be used in metabolic engineering modifications and synthetic biology for the development of efficient metabolic pathways, to improve the nicotine transformation ability of strains; and
(c) development of protein drugs: the above obtained mutant can be used to transform nicotine to eventually produce pseudooxynicotine and have higher catalytic conversion ability than natural proteins, so the mutant can be used for efficient transformation of nicotine in blood, and thereby for developing drugs related to treatment of nicotine addiction.

The concept, specific steps and technical effects of the present invention are further described in conjunction with the accompanying drawings, so as to fully illustrate the objects, features and effects of the present invention.

BRIEF DESCRIPTION OF THE DRAWINGS

FIG. 11 shows the results of comparison of the amino acid sequence of NicA2 with that of the protein of monoamine oxidase family.

DETAILED DESCRIPTION OF THE PREFERRED EMBODIMENTS

Figure 1:
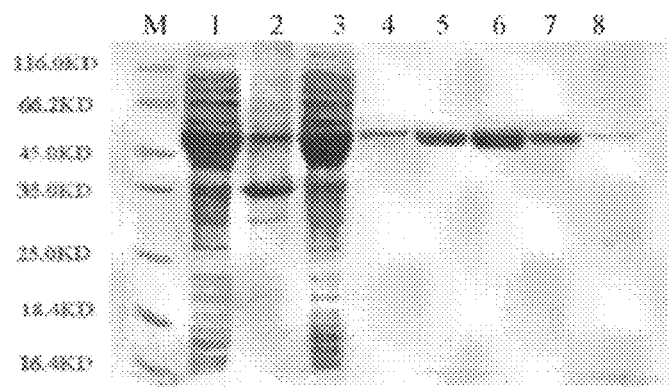
FIG. 1 shows a polyacrylamide gel electrophoresis pattern of purified NicA2 protein according to a preferred embodiment of the present invention, wherein, Lane 1: supernatant after bacteria lysis; Lane 2: precipitate after bacteria lysis; Lane 3: column effluent; Lane 4: 20 mM imidazole washing liquid; Lane 5: 50 mM imidazole washing liquid; Lane 6: 80 mM imidazole eluate; Lane 7: 170 mM imidazole eluate; Lane 8: 300 mM imidazole eluate; and M: protein molecular weight marker.

One aspect of the present invention provides an artificial enzyme manufactured by modifying a sequence of a natural enzyme.

The artificial enzyme used herein should be understood as any enzyme that has been modified for natural enzymes, including genetic engineering modifications, for example, enzyme mutants.

The natural enzyme has the activity for catalyzing the conversion reaction from compound I to compound II as shown by the following formula.

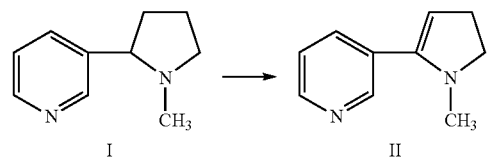

Or, the natural enzyme is nicotine dehydrogenase.

The enzyme described herein having the activity for catalyzing the above reaction should be understood as not only an enzyme which specifically catalyze the above reaction, but also an enzyme which do not specifically catalyze the above reaction, for example, in addition to catalyzing the above reaction, an enzyme that can catalyze the dehydrogenation of 6-hydroxy nicotine (including D type and L type).

The "nicotine dehydrogenase" used herein refers to an enzyme capable of catalyzing the dehydrogenation of a pyrrole ring of a nicotine or nicotine analog (for example, 6-hydroxy nicotine).

The modification comprises: substituting at least one of the amino acids that block product release with amino acids with smaller side chains.

As used herein, "amino acids that block product release" should be understood as any amino acid which can increase product release efficiency or enzyme catalytic efficiency by substitution with other amino acids. For example, if the side chain of an amino acid is located in a product release channel or pathway and the product release efficiency or catalytic efficiency of the enzyme can be increased after the amino acid is substituted with an amino acid with smaller side chains, the amino acid is "an amino acid that blocks product release".

As a preferred particular embodiment, the natural enzyme has one or more of the following features:
1) the amino acid sequence of the natural enzyme includes amino acid sequence with more than 85%, or more than 90%, or more than 95%, or more than 98%, or more than 99% homology to the amino acid sequence shown in SEQ ID NO:1; or the amino acid sequence of the natural enzyme includes the amino acid sequence shown in SEQ ID NO:1; or the amino acid sequence of the natural enzyme is as shown in SEQ ID NO: 1;
2) the natural enzyme is encoded by nucleic acid hybridized with complementary chain of nucleic acid encoding protein with an amino acid sequence shown by SEQ ID NO:1 under a high stringent condition; and 3) the natural enzyme exists in the microorganism *Pseudomonas*.

"Homology" as used herein may refer to an optimal comparison of sequences (nucleotides or amino acids), and the comparison can be performed using a computerized implementation of an algorithm. For example, "homology" associated with a polynucleotide can be obtained by perform analysis with BLASTN version 2.0 based on default parameters. "Homology" associated with a polypeptide (i.e., an amino acid) can be determined by a program (e.g. BLASTP version 2.2.2) based on default parameters. The program compares the polypeptides or fragments being compared (or compares nucleotide fragments), to determine the degree of amino acid identity or similarity.

"Hybridization under conditions of low stringency, medium stringency, high stringency, or very high stringency" as used herein describes the hybridization and washing conditions. The guidance for performing hybridization reactions can refer to Current Protocols in Molecular Biology, John Wiley & Sons, N.Y. (1989), 6.3.1-6.3.6. The document describes the aqueous and non-aqueous methods, and either of which can be used. The specific hybridization conditions herein are as follows: 1) low stringency hybridization conditions: hybridization at about 45° C. in 6× sodium chloride/sodium citrate (SSC), and then washing at least twice at 50° C. in 0.2×SSC, and 0.1% SDS (the washing temperature should be raised to 55° C. for low stringency conditions); 2) medium stringency hybridization conditions: hybridization at about 45° C. in 6×SSC, and then washing once or multiple times at 60° C. in 0.2×SSC, and 0.1% SDS; 3) high stringency hybridization conditions: hybridization at about 45° C. in 6×SSC, and then washing once or multiple times at 65° C. in 0.2×SSC, and 0.1% SDS; and 4) extremely high stringency hybridization conditions: hybridization at 65° C. in 0.5 M sodium phosphate, and 7% SDS, and then washing once or multiple times at 65° C. in 0.2×SSC, and 0.1% SDS. The high stringency conditions (3) are preferred and should be used unless otherwise stated.

As a more preferred particular embodiment, the natural enzyme exists in the *Pseudomonas putida* S16, which has a preservation number CCTCC NO. M 205038, and is preserved in China Center for Type Culture Collection on Apr. 18, 2005. In addition, the strain is also preserved in Deutsche Sammlung von Mikroorganismen und Zellkulturen (DSMZ), with a preservation number of DSM 28022.

As a preferred particular embodiment, the natural enzyme has a product release channel, the amino acid whose side chains are located in the product release channel of natural enzyme includes at least one of the tryptophan, tyrosine, phenylalanine, glutamic acid and methionine; and the modification comprises: substituting at least one of the tryptophan, tyrosine, phenylalanine, glutamic acid and methionine whose side chains are located in product release channel of the natural enzyme with amino acids with smaller side chains.

The "product release channel" used herein should be understood as a path that a product needs to pass from leaving the reactive center of the enzyme to the position at which the catalytic reaction is not affected at all. In general, the reactive center of the enzyme is in the cavity of a three-dimensional structure of an enzyme, which is the same for the artificial enzyme or enzyme disclosed in the invention. The path that a product needs to pass from leaving the reactive center of the enzyme to the position at which the catalytic reaction is not affected at all is at least partially wrapped by some structures. A wrapping degrees are different for different enzymes. Therefore, the path that a product needs to pass from leaving the reactive center of the enzyme to the position at which the catalytic reaction is not affected at all can be understood as a form of "channel".

As used herein, "the side chain of an amino acid being located in the product release channel" is understood as follows: from the perspective of a three-dimensional structure of the enzyme, the side chains of the amino acid have effect, more or less, on the product release efficiency or catalytic efficiency of the enzyme. For example, if the amino acid is substituted with an amino acid with smaller side chains and the product release efficiency or catalytic efficiency of the enzyme can be increased, then the side chains of the amino acid can be considered to locate in the product release channel.

As a preferred particular embodiment, there are at least 9 amino acids whose side chains are located in product release channel of natural enzyme, and the 9 amino acids are selected from tryptophan, tyrosine, phenylalanine, glutamic acid and methionine. As a preferred particular embodiment, the three-dimensional structure of the natural enzyme at least comprises one β-sheet and one α-helix located at the release channel, 3 of the 9 amino acids are located at β-sheet, and according to the relative positions, the 3 amino acids are phenylalanine at position 353, phenylalanine at position 355 and tryptophan at position 364 respectively; and 6 of the 9 amino acids are located at α-helix, and according to the relative positions, the 6 amino acids are the phenylalanine at position 163, tyrosine at position 214, tyrosine at position 218, tyrosine at position 242, methionine at position 246 and glutamic acid at position 249, respectively.

As used herein, the "according to the relative positions" for the amino acid sequence should be understood as follows: the position number of an amino acid in a sequence only represents the relative position of the amino acid. For example, for the foregoing phenylalanine at position 353 and phenylalanine at position 355, it is only indicated that the positions of the former and the latter differ by 2; if a sequence with x amino acids is added at the N-terminus for the entire protein sequence, according to the absolute positions, the position number of the former is 353+x, and the position number of the latter is 355+x; if a sequence with x amino acids is removed at the N-terminus for the entire protein sequence, according to the absolute positions, the position number of the former is 353−x, and the position number of the latter is 355−x; and according to the relative position, the "phenylalanine at position 353" and the "phenylalanine at position 355" should also be understood to include both cases.

In another aspect, the present invention provides an enzyme, and the enzyme has one or more of the following features:

1) the amino acid sequence of the enzyme includes amino acid sequence with more than 85%, or more than 90%, or more than 95%, or more than 98%, or more than 99% homology to the amino acid sequence shown in SEQ ID NO: 2; or the amino acid sequence of the enzyme includes the amino acid sequence shown in SEQ ID NO: 2; or the amino acid sequence of the enzyme is as shown in SEQ ID NO: 2;

2) the enzyme is encoded by nucleic acid hybridized with complementary chain of nucleic acid encoding protein with an amino acid sequence shown by SEQ ID NO:2 under a high stringent condition; and 3) the amino acid sequence of the enzyme includes the amino acid sequence in which the amino acid sequence as shown in SEQ ID NO: 2 is conservatively substituted;

wherein, according to the relative locations, at least one of the amino acids at positions 353, 355 and 364 of the enzyme is a first small-molecular-weight amino acid; at least one of the amino acids at positions 163, 214, 218, 242, 246 and 249 of the enzyme is a second small-molecular-weight amino acid, and the first small-molecular-weight amino acid has a molecular weight less than 140, and the second small-molecular-weight amino acid has a molecular weight less than 110.

As used herein, "being conservatively substituted" should be understood as a substitution of a given amino acid in a polypeptide with another amino acid having similar characteristics. Typically, the following substitutions are considered as conservative substitutions: substituting an aliphatic amino acid such as Ala, Val, Leu, and Ile with another aliphatic amino acid; substituting Ser with Thr, and vice versa; substituting acidic residue such as Asp or Glu with another acidic residue; substituting an amide group-containing residue such as Asn or Gln with another amide group-containing residue; substituting a basic residue such as Lys or Arg with another basic residue; and substituting an aromatic residue such as Phe or Tyr with another aromatic residue.

Functionally equivalent amino acids are generally similar to the amino acids to be substituted in size and/or characteristics (e.g., charge or hydrophobicity). Amino acids with similar properties can be grouped as follows:

(1) hydrophobicity: His, Trp, Trp, Tyr, Phe, Met, Leu, Ile, Val, Ala;
(2) neutral hydrophobicity: Cys, Ser, Thr;
(3) polarity: Ser, Thr, Asn, Gln;
(4) acidic/negatively charged: Asp, Glu;
(5) charged: Asp, Glu, Asn, Lys, His;
(6) basic/positively charged: Asn, Lys, His;
(7) basic: Asn, Gln, His, Lys, Arg;
(8) residues affecting chain orientation: Gly, Pro; and
(9) aromatic: Trp, Tyr, Phe, His.

In another aspect, the present invention provides an enzyme, and the enzyme has the activity for catalyzing the conversion reaction from compound I to compound II as shown by the following formula,

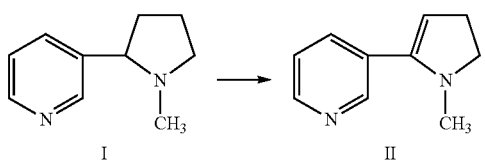

or the enzyme is nicotine dehydrogenase;

The enzyme has a product release channel, wherein the amino acid with a side chain at the narrowest site of the product release channel has a molecular weight of less than 140.

As used herein, "the amino acid with side chains located at the narrowest site of the product release channel" should be understood as the amino acid which is blocked most severely in the path that a product needs to pass from leaving the reactive center of the enzyme to the position at which the catalytic reaction is not affected at all.

The present invention will be further described in combination with particular examples.

The materials used herein can be purchased directly unless otherwise specified. The experimental methods used herein are conventional methods in the art unless otherwise specified.

Example 1: Cloning, Expression and Purification of Wild-Type Nicotine Dehydrogenase (NicA2) and Nitrogen-Terminal-Truncated NicA2 (NicA2Δ20)

1. Cloning of NicA2: The full-length gene sequence of NicA2 protein was obtained through sequencing by Xuping Research Group, as shown in SEQ ID NO: 4. The full-length sequence of NicA2 was amplified from *Pseudomonas putida* S16 bacteria solution (CCTCC No. M 205038) with primers NicA2-F1 and NicA2-R1 using a PCR method, and after digested by NcoI and XhoI, ligated into the pET28a vector with 6 histidine tags at the carbon terminal of the vector. Herein, the primer sequences are:

```
NicA2-F1:
5'-ATACCATGGTGAGTGATAAAACAAAAACAAATGAAG-3';

NicA2-R1:
5'-GTGCTCGAGGCTTAAGAGCTGCTTAACCTCCCTA-3'.
```

2. Expression of NicA2: After being verified through sequencing, the recombinant plasmid pET28α-NicA2 was transformed into the expression vector *E. coli* BL21 (DE3), and single colonies were picked for detection of expression. The colonies with protein expression were amplified and cultured at 37° C. and 220 rpm, and when the $OD_{600}$ of the bacteria solution was 0.6-0.8, induction was performed with 0.2 mM isopropyl thiogalactoside at 16° C. for 16 hours.

3. Purification of NicA2: After the induced bacterial solution was centrifuged, the bacteria were collected and resuspended, crushed at 1500 bar, and centrifuged at a high speed, and then the protein in the supernatant was collected by a pre-filled and balanced Ni-NTA gravity column (purchased from Qiagen, Cat. No. 30430). Non-specifically bound hetero-proteins were removed with 20 mM and 50 mM imidazole, and the target proteins were eluted with 80 mM, 170 mM, and 300 mM imidazole. The target protein was passed through superdex200 column (purchased from GE, model: 28-9909-44) to remove imidazole, and then centrifuged at a speed of not more than 5000 rpm using a 30 KD ultrafiltration tube (MD), so that the target protein was concentrated to 12 mg/mL for use in spotting. The purified protein was verified by polyacrylamide gel electrophoresis, as shown in FIG. 1, and its purity could be over 90%.

4. Cloning, Expression and Purification of NicA2Δ20: The nitrogen-terminal-truncated NicA (NicA2Δ20) was obtained according to the above cloning, expression and purification methods.

Herein, the primers used for cloning were NicA2-F2 and NicA2-R1, and the obtained recombinant plasmid was pET28α-NicA2Δ20.

```
NicA2-F2: ATACCATGGCAGTCGTAACAGCAGGTGTTGCGGGA;

NicA2-R1: GTGCTCGAGGCTTAAGAGCTGCTTAACCTCCCTA.
```

Example 2: Crystallization and Crystal Diffraction of Wild-Type Nicotine Dehydrogenase (NicA2), Nitrogen-Terminal-Truncated NicA2 (NicA2Δ20), and NicA2Δ20-Nicotine Eutectic 1. Crystallization of NicA2: Crystal cultivation was performed for the NicA2 full-length protein at 14° C. by sitting drop method. 1 uL protein and 1 uL crystallization reagent (lower bath) were mixed for dotting on a 48-well plate using Hampton Research protein crystallization kit (Cat. No. HR2-109). After standing for about one week, crystal growth was observed under a microscope; and after standing for two weeks, crystal growth arrest was observed under the microscope. The crystal growth conditions were: Index-65: 0.1 M Ammonium acetate, 0.1 M BIS-TRIS pH 5.5, 17% w/v Polyethylene glycol 10,000; Salt RX2-36: 1.4 M Ammonium tartrate dibasic, 0.1 M Tris pH 8.5.

2. Crystal Diffraction of NicA2: The crystals grown under the condition of Index-65 crystallization had almost no diffraction point by X-ray diffraction, and no crystal grew in the repeated experiments, so optimization for this condition was abandoned. For the crystals grown under the SaltRX2-36 crystallization condition, the resolution of X-ray diffraction was about 3 Å, and the diffraction point had a tail, indicating that the crystals grown under this condition had irregular internal stacking.

The optimization for NicA2 full-length protein crystal after primary screening included the optimization through precipitant concentration and optimization through seed addition, but the crystal diffraction obtained was still poor.

3. Crystallization and Crystal Diffraction of NicA2Δ20: After sequence comparison, 20 amino acids with poor conservation were truncated from the N-terminus. Herein, the sequence comparison with nicotine amineoxidase HZN6 (NCBI accession number: AGH68979.1), (S)-6-hydroxy nicotine-oxidase (NCBI accession number: AGS16700.1) and amine oxidase (NCBI accession number: AEJ14619.1) was performed in NCBI.

Figure 2:
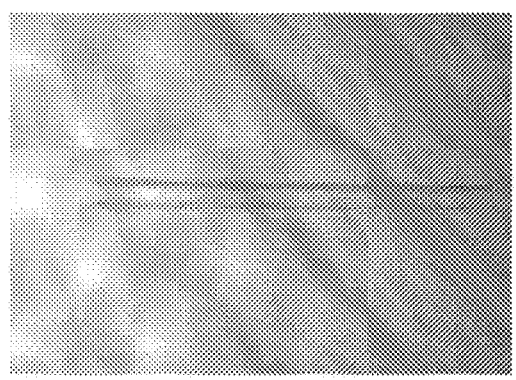
FIG. 2 shows an optimized crystal of a NicA2 protein after being subjected to crystal primary screening, optimization through precipitating agent, seed adding, truncation of amino acid sequence, and adjustment of a ratio of protein to crystallization reagent according to a preferred embodiment of the present invention. The presence of FAD makes the crystal a bright yellow color.

Purified NicA2Δ20 protein was obtained according to the cloning, expression and purification methods in Example 1, and crystal preliminary screening was carried out as described in the above methods. Crystals with improved shape still appeared in the crystallization reagent of SaltRX2-36: 1.4 M Ammonium tartrate dibasic, 0.1 M Tris pH 8.5. The crystal of NicA2Δ20 was subjected to optimization steps such as the precipitant concentration variation, microseeding, and change in ratio of protein and crystallization reagent, etc., to obtain a crystal having an X-ray diffraction resolution of 2.65 Å. Herein, the concentration of the precipitant was optimal at 1.4 M Ammonium tartrate dibasic. The microscopic observation of the crystal was shown in FIG. 2.

4. Selenium Substitution and Crystal Diffraction of NicA2Δ20:

After comparison, the amino acid sequence of NicA2Δ20 had a consistency of only 28% with published proteins in Protein Data Bank (PDB). The NicA2 structure could not be analyzed by simple molecular replacement, so the phase was determined by purifying selenium substituted protein and according to the anomalous scattering of selenium atoms in the self-amino acid, furthermore the structure was analyzed.

The recombinant plasmid pET28α-NicA2Δ20 was transformed into the host *E. coli* B834 (DE3), and the selenium substituted protein was purified by the method in Example 1. The host was a methionine-deficient strain. In an inorganic salt medium, using glucose and yeast inorganic nitrogen sources as nutrients, selenomethionine was added to substitute normal methionine, so seleno-NicA2, i.e. SeMet-NicA2Δ20 could be expressed. The specific expression and purification steps of SeMet-NicA2Δ20 were described in Example 1. After crystal primary screening, SeMet-NicA2Δ20 had crystals with superior appearance in the condition of SaltRX2-36:1.4 M Ammonium tartrate dibasic, 0.1 M Tris pH 8.5. After optimization through the ratio of crystal protein to precipitant, the crystal having an X-ray diffraction resolution of 2.25 Å was obtained.

5. Crystallization and Crystal Diffraction of NicA2Δ20-nicotine Eutectic: NicA2Δ20-nicotine eutectic was obtained by soaking NicA2Δ20 protein crystal in a higher concentration of nicotine solution. The pure nicotine was diluted by a crystal growth buffer (the composition of the buffer as described above) to form a 1 M nicotine mother solution and pH was adjusted to 8.5. The sodium hydrosulfite was dissolved in a crystal growth buffer to 100 mM, and pH was adjusted to 7.0 to form a mother liquor of sodium hydrosulfite. The final concentration of nicotine was 10 mM, and the final concentration of the sodium hydrosulfite was 20 mM in a mixed buffer for soaking crystals. Of which, the sodium hydrosulfite solution produced an oxygen-free environment. The crystal with the best crystal form was taken and quickly soaked into the mixed solution of nicotine and sodium hydrosulfite for 30 seconds, to quickly capture the instant during which NicA2 was bound with the substrate nicotine. The crystals after soaked in nicotine were quickly frozen in liquid nitrogen. Finally, a NicA2Δ20-nicotine crystal having an X-ray diffraction resolution of 2.5 Å was obtained.

Example 3: Structure Elucidation and Analysis of Nicotine Dehydrogenase NicA2

1. Structure Elucidation of NicA2Δ20:

The X-ray diffraction data of the SeMet-NicA2Δ20 crystal obtained in Example 2 was processed by software HKL2000, and the structure of SeMet-NicA2Δ20 was preliminarily elucidated by the phenix program. Using the seleno structure as a template and through isomorphous replacement, the crystal structure was refined by the programs coot and ccp4, and finally the structure of NicA2Δ20 was elucidated.

Figure 3:
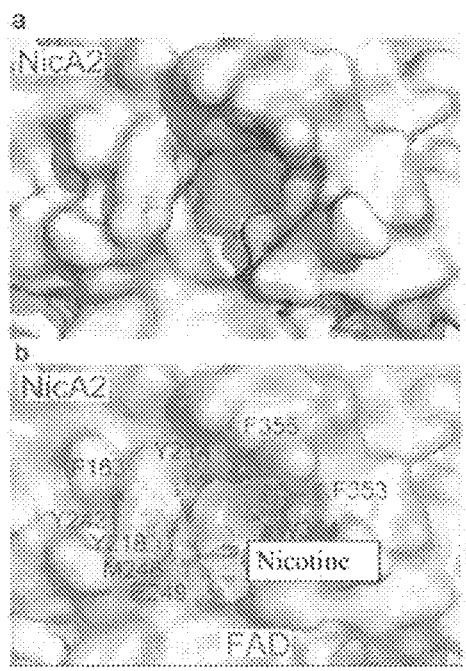
FIG. 3 shows a structural diagram of a NicA2A20-nicotine crystal according to a preferred embodiment of the present invention. a: when viewing the product release channel from above, no product is observed from the outer surface of the crystal structure, indicating that the product is completely embedded by NicA2; b: when viewing the product release channel from above after adjusting the gray scale to transparent, the product release channel is blocked by 9 large amino acids; and c: it is a cross section of the product release channel.
Figure 3:
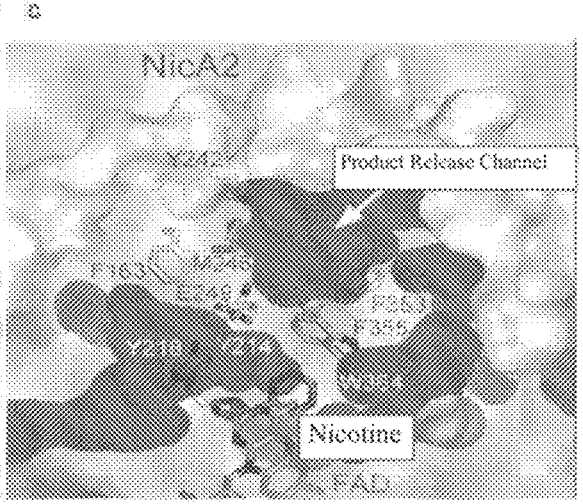

2. Structural Elucidation of NicA2Δ20-nicotine crystal: For the NicA2Δ20-nicotine crystal obtained in Example 2, using the previously elucidated NicA2Δ20 structure as a model and through the molecular replacement method, the structure of NicA2Δ20 and substrate nicotine eutectic was finally elucidated, as shown in FIG. 3.

3. Structural Analysis:

In the article *Crystallographic snapshots of the complete reaction cycle of nicotine degradation by an amine oxidase of the monoamine oxidase (MAO) family* published in PNAS in 2011, the structure of the first dehydrogenase 6-hydroxy-1-nicotine dehydrogenase (6HLNO) in the metabolic nicotine pathway was elucidated in another strain that can efficiently degrade nicotine, and the channels for the substrate 6-hydroxy-nicotine into the catalytic site and releasing the product 6-hydroxy-N-methylmyosmine and 6-hydroxy-pseudooxynicotine were analyzed.

Based on this finding, the amino acid sequences of NicA2 and 6HLNO were compared (NCBI registration No.: YP_007988777.1). Even though the similarity of amino acid sequences is only 28%, the crystal structure of NicA2Δ20 has a certain similarity with the previously reported structure of 6HLNO structure in the *Arthrobacter* sp. nicotine degradation pathway, and the two also differ significantly. The most obvious difference is that diacylglycerol phospholipid is bound to 6HLNO, but this phenomenon does not exist for NicA2Δ20. The a3a and a3b spirals of NicA2Δ20 have a 45-degree rotation compared to the corresponding spiral on 6HLNO. These two α-helixes directly face to the nicotine-binding region, so that NicA2Δ20 has a more tightly packing degree for the substrate nicotine than 6HLNO does for its substrate 6-hydroxy-1-nicotine (6HLN), i.e. the loss of lipid molecules causes NicA2Δ20 to form a more compact structure, such that its nicotine-degrading products of N-methymyosmine and pseudooxynicotine are constrained in a narrow active site pocket within NicA2Δ20.

According to the report of pseudooxynicotine in PNAS (Galina Kachalova et. al, Crystallographic snapshots of the complete reaction cycle of nicotine degradation by an amine oxidase of the monoamine oxidase (MAO) family, [J] *PNAS*, 108 (12): 4800-4805), the corresponding product release channel is found in the NicA2Δ20 structure. Interestingly, the substrate nicotine is completely embedded inside the NicA2Δ20. No trace of nicotine can be found when looking inward either from the channel for substrate incoming or from the product release channel (as shown in a of FIG. 3). Only when the surface gray level of NicA2Δ20 is adjusted to transparency, the nicotine is observed to be deeply embedded in the pocket of the active site (as shown in b of FIG. 3). Through careful analysis of the product release channel, it is found that this channel is blocked by 9 large amino acids: W364 (tryptophan), Y214 (tyrosine), Y218 (tyrosine), F355 (phenylalanine), F353 (phenylalanine), E249 (glutamic acid), F163 (phenylalanine), M246 (methionine) and Y242 (tyrosine) (as shown in b and c of FIG. 3). Therefore, it is speculated that this extremely restraining channel is likely to strongly block the release of the product pseudooxynicotine from NicA2Δ20.

In addition, full-wavelength scanning experiments and gas chromatography (GC) experiments have shown that the characteristics of "complete embedding" and "extreme binding" of NicA2 structure greatly hinder the release of pseudooxynicotine. Herein, the full-wavelength scanning experiments prove that the nicotine can be quickly dehydrogenated under the catalysis of NicA2, and the gas chromatography (GC) experiments prove that the product pseudooxynicotine is released from NicA2 very slowly.

In previous experiments, it is observed that when equimolar substrate nicotine is added to 1 mL of 10 mg/mL NicA2 protein solution, the bright yellow color of the NicA2 protein solution instantly becomes colorless and transparent. In view of that the prosthetic group of NicA2 is FAD and the function of NicA2 is catalytic dehydrogenation of nicotine, it can be considered that an instant process that NicA2 catalyzes the dehydrogenation of nicotine and transfers hydrogen to FAD to oxidize it to form FADH2. That is, the reaction of dehydrogenation of nicotine into pseudooxynicotine is rapidly catalyzed by NicA2. The UV-Scan experiments showed that, after the addition of nicotine to NicA2 solution, the FAD characteristic ultraviolet absorption peaks (375 mm, 450 mm) disappears quickly.

Subsequently, gas chromatography was used to detect the total amount of pseudooxynicotine and the amount of pseudooxynicotine released outside of protein after an equimolar amount of nicotine was added to 1 ml of 10 mg/mL NicA2 solution and reaction was performed for 1.5 hours.

Herein, the pseudooxynicotine was extracted with chloroform-benzyl alcohol for the sample after 1.5 hours of reaction, and the total amount of produced nicotine was quantitatively detected by GC. After repeatedly passing through Ni-NTA column, the NicA2 was considered to be completely bound with the nickel column when the concentration of NicA2 in effluent was detected to be lower than 0.1 mg/mL. The pseudooxynicotine in the effluent was extracted with chloroform-benzyl alcohol, and the amount of pseudooxynicotine released from the NicA2 into solution was quantitatively determined by GC. The results showed that approximately 75% of the pseudooxynicotine remained in the NicA2 protein.

Example 4: Construction of a Nicotine Dehydrogenase Mutant

The positions of the nine large amino acids obtained in Example 3 on the crystal structure of NicA2Δ20 were analyzed, and the amino acid located on the β-sheet was replaced with valine (Vine, V), and the amino acids located on the α-helix were replaced with alanine (Alanine, A). The basic principle for amino acid substitution is to replace the amino acid with a large side chain group with an amino acid having a side chain group as small as possible, at the same time, it should be considered that alanine was the simplest amino acid structure and is also a strong α-helix-maker and the structure of valine is also very simple and is also a strong β-sheet-maker. Finally, F163, Y214, Y218, Y242, M246 and E249 were mutated to alanine, and F353, F355V and W364V were mutated to valine, and the mutant was named as NicA2-M9. By designing the mutated DNA sequence, the above mutation was achieved. The DNA sequence after mutation was shown in SEQ ID NO: 3.

The gene sequence of the above nicotine dehydrogenase mutant NicA2-M9 was synthesized by GENEWIZ Corporation. The synthesized sequence was amplified by a PCR method, and the primers used for amplification were NicA2-F1 and NicA2-R1. The mutant gene fragment and the vector pET28a obtained by amplification were digested with NcoI and XhoI, and ligated with T4 to obtain a recombinant plasmid pET28α-NicA2-M9. After the recombinant plasmid was sequenced and the sequencing result showed a correct sequence, the plasmid was transformed into the host *E. coli* BL21 (DE3) for expression. The purification process of the expressed nicotine dehydrogenase mutant NicA2-M9 was carried out with reference to the wild type NicA2 protein purification method in Example 1.

Figure 4:
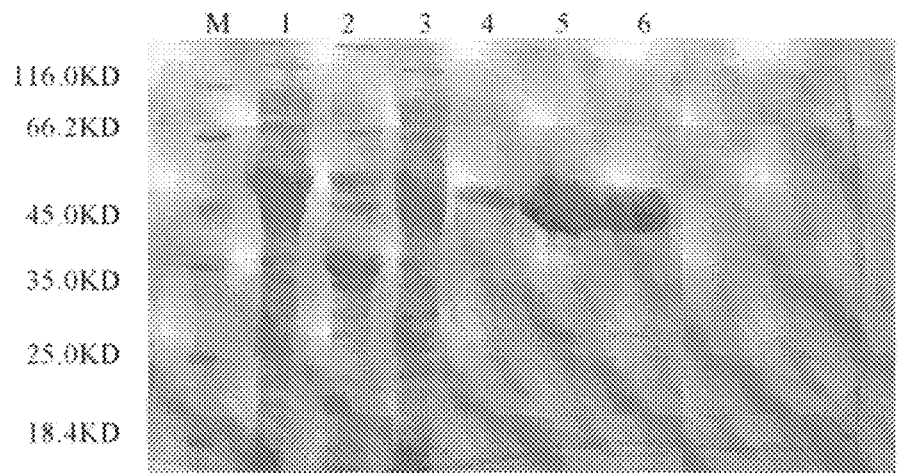
FIG. 4 shows a polyacrylamide gel electrophoresis pattern of purified NicA2-M9 protein according to a preferred embodiment of the present invention, wherein, Lane 1: supernatant after bacteria lysis; Lane 2: precipitate after bacteria lysis; Lane 3: column effluent; Lane 4: 20 mM imidazole lotion; Lane 5: 50 mM imidazole for removing impurity protein; Lane 6: target protein eluted by 170 mM imidazole; and M: protein molecular weight marker.

Samples were taken after the processes of bacteria lysis, the supernatant, precipitate, and column effluent during the purification, 20 mM imidazole, 50 mM imidazole for removing impurity protein and 170 mM imidazole for eluting target protein, and detected by polyacrylamide gel electrophoresis. The results were shown in FIG. 4. The NicA2-M9 protein had a good abundance and the purity was more than 90%, which could meet the requirements of subsequent enzyme activity experiments.

Example 5: Determination and Comparison of Enzyme Activities of Wild-Type Nicotine Dehydrogenase and Nicotine Dehydrogenase Mutants The enzyme activities of the wild type NicA2 and the NicA2 mutant NicA2-M9 were labeled by detecting the amount of the products N-methymyosmine and pseudooxynicotine by using liquid chromatography-mass spectrometry (LC-MS). The LC-MS parameters were as follows: Agilent 1290 LC, EC-C8 column (4.6×100 mm, 1.8 um), and 0.2 mL/min. Under the positive ion mode, the nucleoplasmic ratio (m/z) of N-methymyosmine was 161 and the nucleoplasmic ratio (m/z) of pseudooxynicotine was 179.

The N-methymyosmine and pseudooxynicotine were diluted from the highest concentration of 2 uM to the lowest concentration of 31.25 nM through tiraes ratio dilution, and were loaded to an LC-MS instrument, and the peaks with nucleoplasmic ratios of 161 and 179 were selected. The area of the peak automatically annotated from the instrument was recorded. The standard curves of the two products were plotted using the software OriginPro8.

Figure 5:
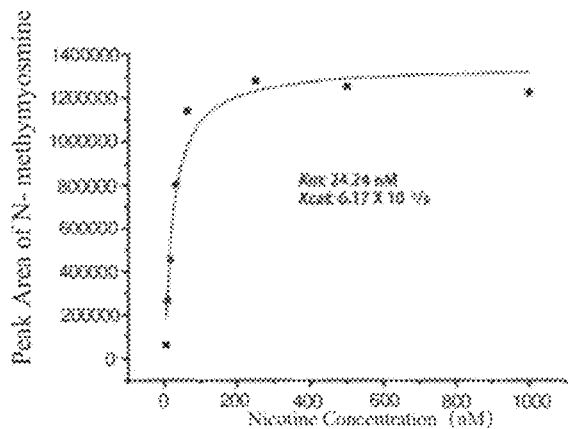
FIG. 5 shows a Michaelis-Menten equation curve for the process of the production of N-methylmyosmine by catalyzing nicotine with wild type NicA2 according to a preferred embodiment of the present invention.
Figure 6:
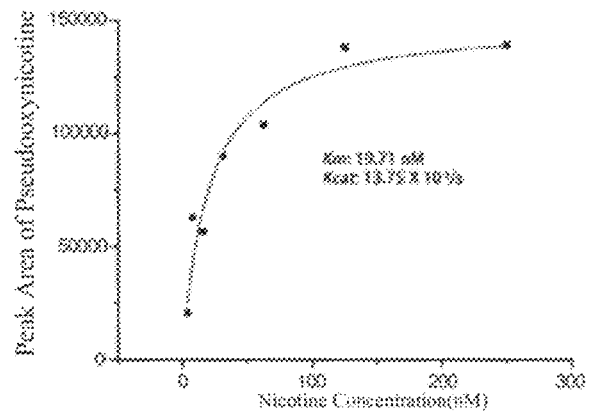
FIG. 6 shows a Michaelis-Menten equation curve for the process of the production of pseudooxynicotine by catalyzing nicotine with wild type NicA2 according to a preferred embodiment of the present invention.

1. Determination of Wild-Type Nicotine Dehydrogenase Activity:

The final concentration of the immobilized NicA2 wild-type protein was 10 nM, and the concentration of the substrate nicotine was diluted from the highest concentration of 2 uM to the lowest concentration of 12.5 nM. The protein and substrate were incubated at 30° C. for 20 minutes, and the reaction was inactivated by 2.5 times volume of acetonitrile. The protein precipitate was removed by centrifuging for 2 min at 12,000 rpm, and the obtained sample was loaded to a LC-MS instrument. The peaks with nucleoplasmic ratios at 161 and 179 were selected, and the peak area automatically annotated from the instrument was recorded. The Michaelis-Menten equation curve was plotted by OriginPro 8, as shown in FIG. 5 and FIG. 6.

The $K_m$ and $k_{cat}$ values for producing N-methylmyosmine and pseudooxynicotine by reaction through NicA2 wild-type nicotine was calculated by combining the standard curve of the product. The $K_m$ and $k_{cat}$ values for producing N-methylmyosmine by reaction through NicA2 wild-type nicotine reaction were 24.24 nM and $6.17 \times 10^{-3}$/s, respectively; and the $K_m$ and $k_{cat}$ values for producing pseudooxynicotine were 19.71 nM and $13.75 \times 10^{-3}$/s, respectively.

Figure 7:
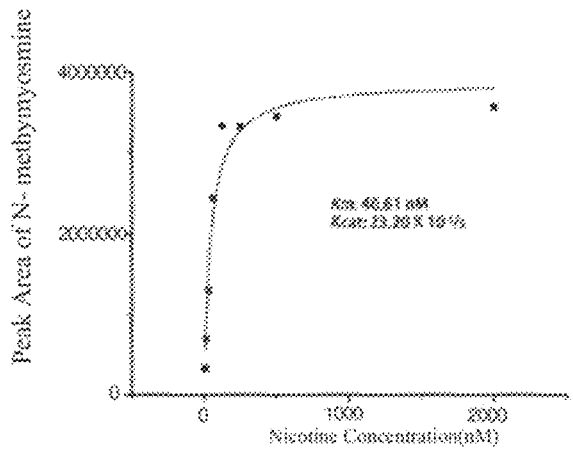
FIG. 7 shows a Michaelis-Menten equation curve for the process of the production of N-methylmyosmine by catalyzing nicotine with NicA2-M9 according to a preferred embodiment of the present invention.
Figure 8:
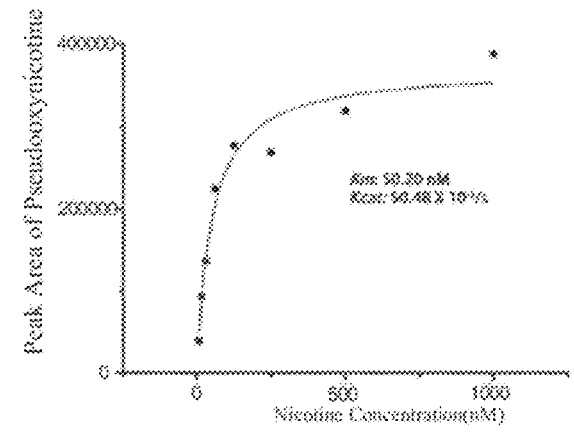
FIG. 8 shows a Michaelis-Menten equation curve for the process of the production of pseudooxynicotine by catalyzing nicotine with NicA2-M9 according to a preferred embodiment of the present invention.

2. Determination of Nicotine Dehydrogenase Mutant Enzyme Activity:

The determination method of nicotine dehydrogenase mutant NicA2-M9 enzyme activity was the same as that of wild type NicA2 enzyme activity. The final concentration of immobilized NicA2-M9 protein was 10 nM, and the concentration of substrate nicotine was diluted from the highest concentration of 2 uM to the lowest concentration of 12.5 nM through tiraes ratio dilution. The protein and substrate were incubated at 30° C. for 20 minutes, and the reaction was inactivated by 2.5 times volume of acetonitrile. The protein precipitate was removed by centrifuging for 2 min at 12,000 rpm, and the obtained sample was loaded to a LC-MS instrument. The peaks with the nucleoplasmic ratios of 161 and 179 were selected, and the peak area automatically annotated from the instrument was recorded. The Michaelis-Menten equation curve was plotted by OriginPro 8, as shown in FIG. 7 and FIG. 8.

Based on the standard curve of the product, the $K_m$ and $k_{cat}$ values for producing N-methylmyosmine and pseudooxynicotine by catalyzing nicotine with NicA2-M9 were calculated. The $K_m$ and $k_{cat}$ values for producing N-methylmyosmine by catalyzing nicotine with NicA2-M9 were 46.61 nM and $23.20 \times 10^{-3}$/s, respectively.

3. Comparison

Table 1 shows the $K_m$ and $k_{cat}$ values for producing N-methylmyosmine and pseudooxynicotine by catalyzing substrate with wild type NicA2 and NicA2-M9. By comparison, it shows that the $K_m$ for producing N-methylmyosmine by NicA2-M9 catalysis is 1.96 times of that of wild type NicA2, and the $K_m$ for producing pseudooxynicotine by NicA2-M9 catalysis is 2.5 times of that of wild type NicA2. However, the $k_{cat}$ for producing N-methylmyosmine by NicA2-M9 catalysis is 3.76 times of that of wild type NicA2, and the $k_{cat}$ for producing pseudooxynicotine by NicA2-M9 catalysis is 3.67 times of that of wild type NicA2, which further demonstrates that the substitution of a bulky amino acid with an amino acid with simple side chains can effectively accelerate the release of the product pseudooxynicotine and increase the efficiency of the reaction.

TABLE 1

The reaction rate constants for catalyzing nicotine reactions with NicA2 wild-type and NicA2 mutants

|  |  | m/z 161 | m/z 179 |
|---|---|---|---|
| $K_m$ | NicA2 wild type | 24.24 nM | 19.71 nM |
|  | NicA2 mutant | 46.61 nM | 50.20 nM |
| $k_{cat}$ | NicA2 wild type | $6.17 \times 10^{-3}$/s | $13.75 \times 10^{-3}$/s |
|  | NicA2 mutant | $23.20 \times 10^{-3}$/s | $50.48 \times 10^{-3}$/s |

Example 6: Comparative Analysis of Nicotine Dehydrogenase Mutant Properties and Blood Concentration of Nicotine The results of Example 5 indicates that the rate for catalyzing nicotine by NicA2-M9 is much higher than that of NicA2 wild-type protein, while the affinity of NicA2-M9 for nicotine is slightly weaker than that of NicA2 wild-type protein. Subsequently, the affinity of NicA2-M9 for nicotine ($K_m$) is compared with the concentration of nicotine in the blood. As shown in Table 3, it is found that even if NicA2-M9 has a slightly weaker affinity for nicotine than wild type NicA2, the $K_m$ of catalyzing nicotine by NicA2-M9 is lower than most concentrations of nicotine in the blood.

TABLE 2

The affinity of NicA2 mutant for nicotine and the highest concentration of nicotine in the blood

| Affinity of NicA2 mutant for nicotine ($K_m$) | The highest concentration of nicotine in the blood |
|---|---|
| 96.81 nM | 162 nM-370 nM |

Example 7: Modification of Original Metabolic Pathway by Nicotine Dehydrogenase Mutant The wild type NicA2 and NicA2-M9 gene sequences were ligated into shuttle plasmid pME6032 to obtain pME6032-NicA2 plasmid and pME6032-NicA2-M9 plasmid. Herein, the pME6032 plasmid can respond well to the induction of isopropylthiogalactoside. The recombinant plasmid was transformed into *Pseudomonas putida* S16 through electroporation, and simultaneously into the empty pME6032 plasmid and the pME6Q32-NicA2-M9+pNAO plasmid ligated with NicA2-M9 gene sequences and recombinant fragments of protein pseudooxynicotine AO gene sequences whose downstream catalyzes pseudooxynicotine (pseudooxynicotine AO can efficiently catalyze pseudooxynicotine), which were used as two groups of controls, respectively.

*Pseudomonas putida* S16 transformed with the above four plasmids was cultured in an inorganic salt medium containing nicotine as the sole carbon and nitrogen source, and when the $OD_{600}$ value was 0.6, 3 mg/mL nicotine and 0.8 mM isopropylthiogalactoside were added to induce protein expression. 2 mL of bacterial supernatant induced for each sample for 0-5 hours was collected, after lyophilization, the pseudooxynicotine was extracted with benzyl alcohol-chloroform and loaded into a gas chromatograph. The amount of pseudooxynicotine was measured by a pseudoxynicotine standard curve drawn previously.

Figure 9:
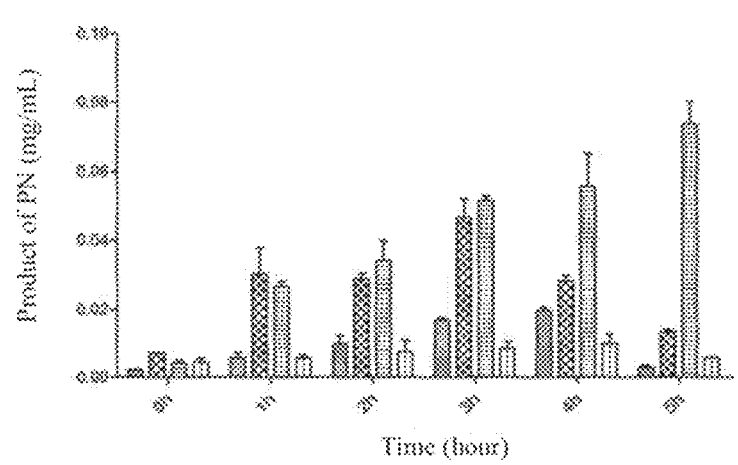
FIG. 9 shows the release amount of pseudooxynicotine detected by GC according to a preferred embodiment of the present invention.

As shown in FIG. 9, the experimental results demonstrates that, compared with the cases of transformation into pME6032 empty plasmid and pME6032-NicA2 plasmid through electroporation, the case of transformation into the pME6032-NicA2-M9 plasmid through electroporation (i.e. as shown in s16(NicA2-9 MT) in FIG. 9) shows significantly increase in the release amount of pseudooxynicotine. When NicA2-M9 is recombined with pseudooxynicotine AO (i.e. as shown in s16(NicA2-9 MT+pNAO) in FIG. 9), the pseudooxynicotine AO degrades the pseudooxynicotine, which significantly reduces the release amount of pseudooxynicotine. It further confirms that the increased release amount of pseudooxynicotine is caused by modification of NicA2 protein.

Example 8

Similar to Example 4, the positions of the nine large amino acids obtained in Example 3 on the crystal structure of NicA2 Δ20 were analyzed, and the following mutations were made:
(1) F353, F355 and W364 were mutated to valine, and the mutant was named as NicA2-M3V, and the amino acid sequence of which was as shown in SEQ ID NO: 8;
(2) F353, F355 and W364 were mutated to alanine, and the mutant was named as NicA2-M3A, and the amino acid sequence of which was as shown in SEQ ID NO: 9;
(3) F353, F355 and W364 were mutated to valine, Y214 and Y218 were mutated to alanine, and the mutant was named as NicA2-M5, and the amino acid sequence of which was as shown in SEQ ID NO: 10; and
(4) F353, F355 and W364 were mutated to valine, Y214, Y218, F163 and E249 were mutated to alanine, and the mutant was named as NicA2-M7, and the amino acid sequence of which was as shown in SEQ ID NO: 11.

Figure 10:
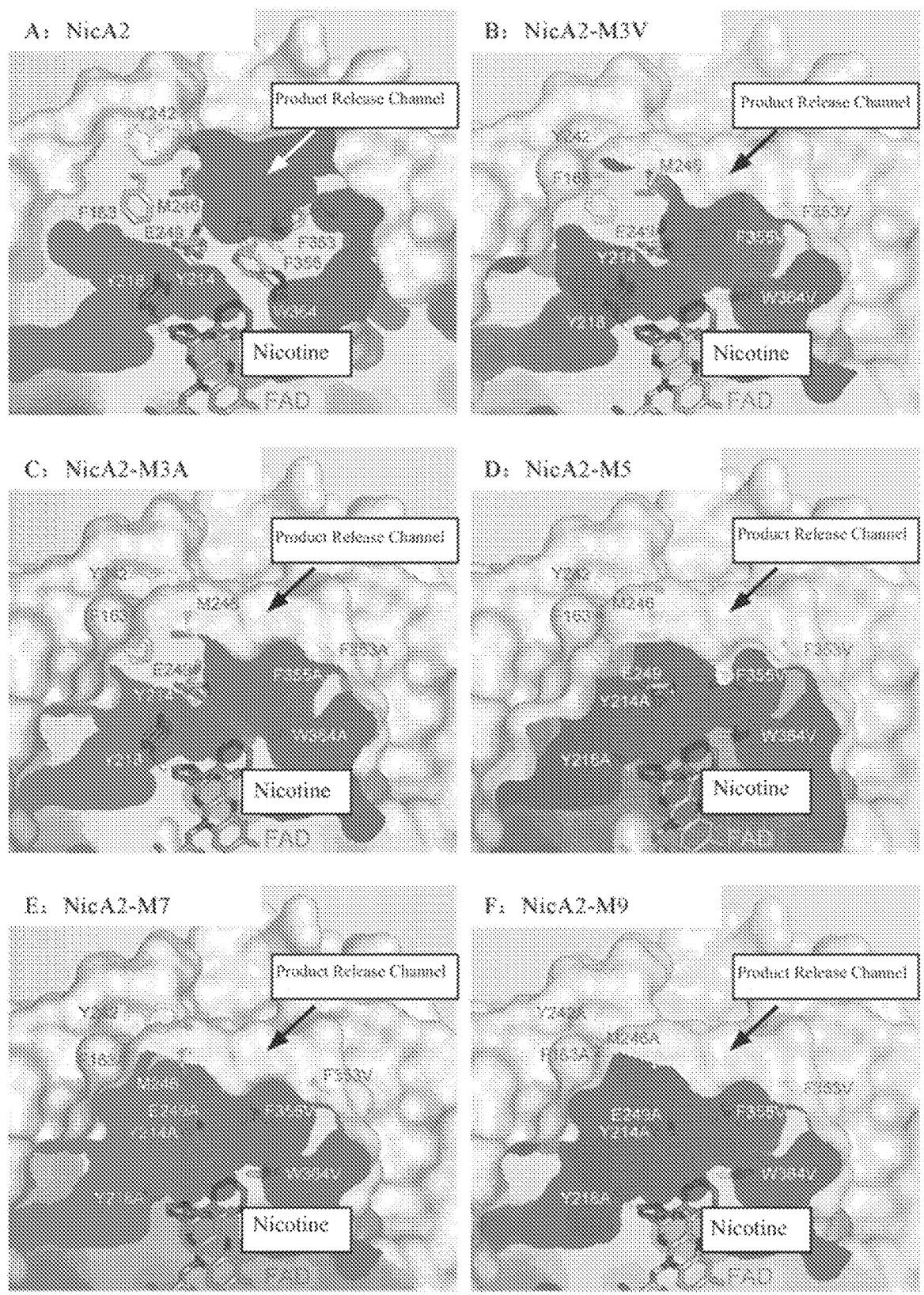
FIG. 10 shows cross-sectional views of product release channels of five NicA2 mutants generated in a particular embodiment of the present invention and wild type NicA2, wherein, A: wild type NicA2; B: NicA2-M3V mutant; C: NicA2-M3A mutant; D: NicA2-M5 mutant; E: NicA2-M7 mutant; and F: NicA2-M9 mutant.

As can be seen from A of FIG. 10, the product release channel of wild-type NicA2 is blocked by the nine large amino acids described above. For the various combinations of mutations for the nine large amino acids, as shown from FIG. 10, the product release channels of NicA2-M3V mutant (B), NicA2-M3A mutant (C), NicA2-M5 mutant (D), NicA2-M7 mutant (E) and NicA2-M9 mutant (F) are broadened to varying degrees. In combination with the above related activity experiments for the NicA2-M9 mutant, those skilled in the art will appreciate that, when the large amino acids that block product release are replaced with small amino acids for the above mutations, it can accelerate the product release and improve the reaction efficiency.

It will also be apparent to those skilled in the art that, as long as large amino acids that block product release are partially or wholly replaced by smaller amino acids, it can improve the product release rate for NicA2. The mutations listed in the examples are merely illustrative.

Example 9: Commonality of Phenomenon that Nicotine Dehydrogenase Contains 9 Large Amino Acids that Hinder the Release of Substrates Among Members of the Monoamine Oxidase Family The amino acid sequence of NicA2 was compared with the amino acid sequence of 10 amino acids including monoamine oxidase A (MAO-A) and monoamine oxidase B (MAO-B) in the monoamine oxidase family using the sequence comparison software Vector NTI, and the results were shown in FIG. 11. It was found that the nine large amino acids in NicA2 that blocked the release of the substrate had certain conservation in family members (as shown in the arrows in FIG. 11). The amino acid comparison revealed that amino acids in family members corresponding to the nine large amino acids in NicA2 that blocked the release of the substrate were almost amino acids with bulky side chains.

The structures of monoamine oxidase A and monoamine oxidase B are reported, and structural analysis suggests that their substrates are also embedded in the "cave" consisting of aromatic amino acids, which is very similar to NicA2 (*J. Mol. Biol.* 338, 103-114; *Proc. Natl. Acad. Sci. USA* 100, 9750-9755). Base on the above content, we can reasonably explain the phenomenon of blockage by large amino acids in the monoamine oxidase A and monoamine oxidase B product channels. Monoamine oxidase is a mitochondrial transmembrane protein that is responsible for the transmission of neurotransmitters. The important substrate for monoamine oxidase A is serotonin, and the oxidase A catalyzes the further conversion of serotonin to melatonin. It is worth noting that serotonin has high content in cerebral cortex and synapses, which can excite the body, while melatonin is a tranquilizer and a substance that induces sleep; the important substrate for monoamine oxidase B is tetrahydropyridine, and its catalysis product is a neurotoxin that generates Parkinson's disease.

Similar to NicA2, the substrates for monoamine oxidase A and monoamine oxidase B and especially the products are tiny but functionally important small molecules. It is conceivable that the embedding of product release channel with large amino acids by proteins is actually a controllable release mechanism for the product.

The preferred embodiments of the present invention have been described in detail above. Those skilled in the art can make many modifications and variations without creative work according to the conception of the invention. Therefore, any technical solution that can be obtained by those skilled in the art based on the prior art by logic analysis, reasoning or limited experimentation should be within the scope of protection determined by the appended claims.

The invention claimed is:

1. An enzyme, the enzyme having the activity for catalyzing the conversion reaction from compound I to compound II as shown by the following formula:

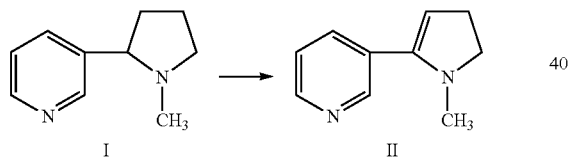

wherein the enzyme has an amino acid sequence as shown in SEQ ID NO:2, or as shown in SEQ ID NO:8, or as shown in SEQ ID NO:9, or as shown in SEQ ID NO:10, or as shown in SEQ ID NO:11.

* * * * *

SEQUENCE LISTING

```
<160> NUMBER OF SEQ ID NOS: 21

<210> SEQ ID NO 1
<211> LENGTH: 482
<212> TYPE: PRT
<213> ORGANISM: Pseudomonas putida S16

<400> SEQUENCE: 1

Met Ser Asp Lys Thr Lys Thr Asn Glu Gly Phe Ser Arg Arg Ser Phe
1               5                   10                  15
```

Ile Gly Ser Ala Ala Val Val Thr Ala Gly Val Ala Gly Leu Gly Ala
                20                  25                  30

Ile Asp Ala Ala Ser Ala Thr Gln Lys Thr Asn Arg Ala Ser Thr Val
                35                  40                  45

Lys Gly Gly Phe Asp Tyr Asp Val Val Val Gly Gly Gly Phe Ala
50                  55                  60

Gly Ala Thr Ala Ala Arg Glu Cys Gly Leu Gln Gly Tyr Arg Thr Leu
65                  70                  75                  80

Leu Leu Glu Ala Arg Ser Arg Leu Gly Arg Thr Phe Thr Ser Arg
                85                  90                  95

Phe Ala Gly Gln Glu Ile Glu Phe Gly Gly Ala Trp Val His Trp Leu
                100                 105                 110

Gln Pro His Val Trp Ala Glu Met Gln Arg Tyr Gly Leu Gly Val Val
                115                 120                 125

Glu Asp Pro Leu Thr Asn Leu Asp Lys Thr Leu Ile Met Tyr Asn Asp
130                 135                 140

Gly Ser Val Glu Ser Ile Ser Pro Asp Glu Phe Gly Lys Asn Ile Arg
145                 150                 155                 160

Ile Ala Phe Glu Lys Leu Cys His Asp Ala Trp Glu Val Phe Pro Arg
                165                 170                 175

Pro His Glu Pro Met Phe Thr Glu Arg Ala Arg Glu Leu Asp Lys Ser
                180                 185                 190

Ser Val Leu Asp Arg Ile Lys Thr Leu Gly Leu Ser Arg Leu Gln Gln
                195                 200                 205

Ala Gln Ile Asn Ser Tyr Met Ala Leu Tyr Ala Gly Glu Thr Thr Asp
                210                 215                 220

Lys Phe Gly Leu Pro Gly Val Leu Lys Leu Phe Ala Cys Gly Gly Trp
225                 230                 235                 240

Asn Tyr Asp Ala Phe Met Asp Thr Glu Thr His Tyr Arg Ile Gln Gly
                245                 250                 255

Gly Thr Ile Gly Leu Ile Asn Ala Met Leu Thr Asp Ser Gly Ala Glu
                260                 265                 270

Val Arg Met Ser Val Pro Val Thr Ala Val Glu Gln Val Asn Gly Gly
                275                 280                 285

Val Lys Ile Lys Thr Asp Asp Glu Ile Ile Thr Ala Gly Val Val
                290                 295                 300

Val Met Thr Val Pro Leu Asn Thr Tyr Lys His Ile Gly Phe Thr Pro
305                 310                 315                 320

Ala Leu Ser Lys Gly Lys Gln Arg Phe Ile Lys Glu Gly Gln Leu Ser
                325                 330                 335

Lys Gly Ala Lys Leu Tyr Val His Val Lys Gln Asn Leu Gly Arg Val
                340                 345                 350

Phe Ala Phe Ala Asp Glu Gln Gln Pro Leu Asn Trp Val Gln Thr His
                355                 360                 365

Asp Tyr Ser Asp Glu Leu Gly Thr Ile Leu Ser Ile Thr Ile Ala Arg
                370                 375                 380

Lys Glu Thr Ile Asp Val Asn Asp Arg Asp Ala Val Thr Arg Glu Val
385                 390                 395                 400

Gln Lys Met Phe Pro Gly Val Glu Val Leu Gly Thr Ala Ala Tyr Asp
                405                 410                 415

Trp Thr Ala Asp Pro Phe Ser Leu Gly Ala Trp Ala Ala Tyr Gly Val
                420                 425                 430

```
Gly Gln Leu Ser Arg Leu Lys Asp Leu Gln Ala Ala Glu Gly Arg Ile
            435                 440                 445

Leu Phe Ala Gly Ala Glu Thr Ser Asn Gly Trp His Ala Asn Ile Asp
450                 455                 460

Gly Ala Val Glu Ser Gly Leu Arg Ala Gly Arg Glu Val Lys Gln Leu
465                 470                 475                 480

Leu Ser

<210> SEQ ID NO 2
<211> LENGTH: 482
<212> TYPE: PRT
<213> ORGANISM: Pseudomonas putida S16

<400> SEQUENCE: 2

Met Ser Asp Lys Thr Lys Thr Asn Glu Gly Phe Ser Arg Arg Ser Phe
1               5                   10                  15

Ile Gly Ser Ala Ala Val Val Thr Ala Gly Val Ala Gly Leu Gly Ala
                20                  25                  30

Ile Asp Ala Ala Ser Ala Thr Gln Lys Thr Asn Arg Ala Ser Thr Val
            35                  40                  45

Lys Gly Gly Phe Asp Tyr Asp Val Val Val Gly Gly Gly Phe Ala
    50                  55                  60

Gly Ala Thr Ala Ala Arg Glu Cys Gly Leu Gln Gly Tyr Arg Thr Leu
65                  70                  75                  80

Leu Leu Glu Ala Arg Ser Arg Leu Gly Gly Arg Thr Phe Thr Ser Arg
                85                  90                  95

Phe Ala Gly Gln Glu Ile Glu Phe Gly Gly Ala Trp Val His Trp Leu
            100                 105                 110

Gln Pro His Val Trp Ala Glu Met Gln Arg Tyr Gly Leu Gly Val Val
        115                 120                 125

Glu Asp Pro Leu Thr Asn Leu Asp Lys Thr Leu Ile Met Tyr Asn Asp
130                 135                 140

Gly Ser Val Glu Ser Ile Ser Pro Asp Glu Phe Gly Lys Asn Ile Arg
145                 150                 155                 160

Ile Ala Ala Glu Lys Leu Cys His Asp Ala Trp Glu Val Phe Pro Arg
                165                 170                 175

Pro His Glu Pro Met Phe Thr Glu Arg Ala Arg Glu Leu Asp Lys Ser
            180                 185                 190

Ser Val Leu Asp Arg Ile Lys Thr Leu Gly Leu Ser Arg Leu Gln Gln
        195                 200                 205

Ala Gln Ile Asn Ser Ala Met Ala Leu Ala Ala Gly Glu Thr Thr Asp
    210                 215                 220

Lys Phe Gly Leu Pro Gly Val Leu Lys Leu Phe Ala Cys Gly Gly Trp
225                 230                 235                 240

Asn Ala Asp Ala Phe Ala Asp Thr Ala Thr His Tyr Arg Ile Gln Gly
                245                 250                 255

Gly Thr Ile Gly Leu Ile Asn Ala Met Leu Thr Asp Ser Gly Ala Glu
            260                 265                 270

Val Arg Met Ser Val Pro Val Thr Ala Val Glu Gln Val Asn Gly Gly
        275                 280                 285

Val Lys Ile Lys Thr Asp Asp Glu Ile Ile Thr Ala Gly Val Val
    290                 295                 300

Val Met Thr Val Pro Leu Asn Thr Tyr Lys His Ile Gly Phe Thr Pro
305                 310                 315                 320
```

Ala Leu Ser Lys Gly Lys Gln Arg Phe Ile Lys Glu Gly Gln Leu Ser
            325                 330                 335

Lys Gly Ala Lys Leu Tyr Val His Val Lys Gln Asn Leu Gly Arg Val
        340                 345                 350

Val Ala Val Ala Asp Glu Gln Gln Pro Leu Asn Val Val Gln Thr His
    355                 360                 365

Asp Tyr Ser Asp Glu Leu Gly Thr Ile Leu Ser Ile Thr Ile Ala Arg
370                 375                 380

Lys Glu Thr Ile Asp Val Asn Asp Arg Asp Ala Val Thr Arg Glu Val
385                 390                 395                 400

Gln Lys Met Phe Pro Gly Val Glu Val Leu Gly Thr Ala Ala Tyr Asp
                405                 410                 415

Trp Thr Ala Asp Pro Phe Ser Leu Gly Ala Trp Ala Ala Tyr Gly Val
            420                 425                 430

Gly Gln Leu Ser Arg Leu Lys Asp Leu Gln Ala Ala Glu Gly Arg Ile
        435                 440                 445

Leu Phe Ala Gly Ala Glu Thr Ser Asn Gly Trp His Ala Asn Ile Asp
    450                 455                 460

Gly Ala Val Glu Ser Gly Leu Arg Ala Gly Arg Glu Val Lys Gln Leu
465                 470                 475                 480

Leu Ser

<210> SEQ ID NO 3
<211> LENGTH: 975
<212> TYPE: DNA
<213> ORGANISM: Pseudomonas putida S16

<400> SEQUENCE: 3
attcgaatag ctgctgaaaa gctttgtcac gatgcctggg aagtatttcc tcgtccgcat     60
gagccgatgt ttactgagcg cgctcgggaa ttggataaat cttctgttct tgatcgcatc    120
aaaactttgg gcttaagtcg gctgcaacag gctcaaatca atagtgctat ggccttggct    180
gcaggtgaga caactgacaa atttggcctg cctggtgtac ttaagttgtt tgcatgcggc    240
ggttggaacg ctgacgcctt cgcggacact gcaactcatt atagaattca aggggggcacg    300
ataggcctca ttaatgcaat gttgaccgat agcggtgccg aggtccgcat gtctgtgccc    360
gtcactgctg ttgagcaagt caatggtggc gtcaaaatca agaccgacga cgacgaaatt    420
attaccgccg gagtggtcgt aatgacagtt ccactcaata cgtataaaca tatcggtttt    480
acgcctgccc tttctaaagg taaacaacga ttcatcaaag aggggcagct tagcaaaggt    540
gctaagcttt atgttcatgt taagcagaat ctcggacggg ttgttgcggt tgcggatgaa    600
cagcaacctt taaacgtggt ccagacgcac gattacagcg acgagttggg gacaatactg    660
tcgatcacca tcgctcgcaa agaaacaatt gatgtgaatg accgagatgc tgtaactcgc    720
gaagttcaaa aaatgtttcc gggtgttgag gttcttggta cagcggctta cgactggaca    780
gctgatccat ttccttgggg ggcatgggcg gcttatggag taggtcaact aagtcgtctc    840
aaagatctac aggcggctga aggacgtatt ttatttgcag gagctgaaac cagtaacggt    900
tggcacgcga atatcgatgg tgctgttgaa agtggactac gtgccggtag ggaggttaag    960
cagctcttaa gctag                                                    975

<210> SEQ ID NO 4
<211> LENGTH: 1449
<212> TYPE: DNA
<213> ORGANISM: Pseudomonas putida S16

<400> SEQUENCE: 4

```
atgagtgata aaacaaaaac aaatgaaggc tttagccgca ggtctttat cggaagcgcg        60
gcagtcgtaa cagcaggtgt tgcgggattg ggagctattg atgcggcttc ggctacgcaa       120
aaaacgaacc gagcaagcac cgtcaaaggt ggcttcgatt acgatgtggt agtagttggt       180
ggagggtttg ctggcgcgac agccgcccgt gaatgtggtt tgcagggtta cgaacgctt        240
ttattggaag cgaggtcccg cctaggtggt cgtacgttta cctcgcgctt tgcaggtcaa       300
gaaattgaat ttggcggggc atgggtgcac tggctgcagc cgcatgtttg gcagaaatg        360
cagcgttacg gtctgggtgt agtggaagat ccacttacta atttagataa aaccttaatc       420
atgtataacg acggaagcgt cgaaagtatt tcgcccgatg aatttggcaa aacattcga        480
atagcttttg aaaagctttg tcacgatgcc tgggaagtat ttcctcgtcc gcatgagccg       540
atgtttactg agcgcgctcg ggaattggat aaatcttctg ttcttgatcg catcaaaact       600
ttgggcttaa gtcggctgca acaggctcaa atcaatagtt acatggcctt gtatgcaggt       660
gagacaactg acaaatttgg cctgcctggt gtacttaagt tgtttgcatg cggcggttgg       720
aactatgacg ccttcatgga cactgaaact cattatagaa ttcaagggg cacgataggc        780
ctcattaatg caatgttgac cgatagcggt gccgaggtcc gcatgtctgt gcccgtcact       840
gctgttgagc aagtcaatgg tggcgtcaaa atcaagaccg acgacgacga aattattacc       900
gccggagtgg tcgtaatgac agttccactc aatacgtata acatatcgg ttttacgcct        960
gccctttcta aggtaaaca acgattcatc aaagaggggc agcttagcaa aggtgctaag       1020
ctttatgttc atgttaagca gaatctcgga cgggttttg cgtttgcgga tgaacagcaa       1080
cctttaaact gggtccagac gcacgattac agcgacgagt tggggacaat actgtcgatc       1140
accatcgctc gcaaagaaac aattgatgtg aatgaccgag atgctgtaac tcgcgaagtt      1200
caaaaaatgt ttccgggtgt tgaggttctt ggtacagcgg cttacgactg gacagctgat      1260
ccattttcct tggggggcatg gcggcttat ggagtaggtc aactaagtcg tctcaaagat       1320
ctacaggcgg ctgaaggacg tattttattt gcaggagctg aaaccagtaa cggttggcac       1380
gcgaatatcg atggtgctgt tgaaagtgga ctacgtgccg gtagggaggt taagcagctc      1440
ttaagctag                                                              1449
```

<210> SEQ ID NO 5
<211> LENGTH: 36
<212> TYPE: DNA
<213> ORGANISM: Artificial Sequence
<220> FEATURE:
<223> OTHER INFORMATION: NicA2-F1

<400> SEQUENCE: 5

```
ataccatggt gagtgataaa acaaaaacaa atgaag                                  36
```

<210> SEQ ID NO 6
<211> LENGTH: 34
<212> TYPE: DNA
<213> ORGANISM: Artificial Sequence
<220> FEATURE:
<223> OTHER INFORMATION: NicA2-R1

<400> SEQUENCE: 6

```
gtgctcgagg cttaagagct gcttaacctc ccta                                    34
```

<210> SEQ ID NO 7

```
<211> LENGTH: 35
<212> TYPE: DNA
<213> ORGANISM: Artificial Sequence
<220> FEATURE:
<223> OTHER INFORMATION: NicA2-F2

<400> SEQUENCE: 7
ataccatggc agtcgtaaca gcaggtgttg cggga                              35

<210> SEQ ID NO 8
<211> LENGTH: 482
<212> TYPE: PRT
<213> ORGANISM: Pseudomonas putida S16

<400> SEQUENCE: 8
```

| | | | | | | | | | | | | | | |
|---|---|---|---|---|---|---|---|---|---|---|---|---|---|---|
| Met | Ser | Asp | Lys | Thr | Lys | Thr | Asn | Glu | Gly | Phe | Ser | Arg | Arg | Ser | Phe |
| 1 | | | | 5 | | | | | 10 | | | | | 15 | |

Ile Gly Ser Ala Ala Val Val Thr Ala Gly Val Ala Gly Leu Gly Ala
            20                  25                  30

Ile Asp Ala Ala Ser Ala Thr Gln Lys Thr Asn Arg Ala Ser Thr Val
        35                  40                  45

Lys Gly Gly Phe Asp Tyr Asp Val Val Val Gly Gly Gly Phe Ala
 50                  55                  60

Gly Ala Thr Ala Ala Arg Glu Cys Gly Leu Gln Gly Tyr Arg Thr Leu
65                  70                  75                  80

Leu Leu Glu Ala Arg Ser Arg Leu Gly Gly Arg Thr Phe Thr Ser Arg
                85                  90                  95

Phe Ala Gly Gln Glu Ile Glu Phe Gly Gly Ala Trp Val His Trp Leu
            100                 105                 110

Gln Pro His Val Trp Ala Glu Met Gln Arg Tyr Gly Leu Gly Val Val
        115                 120                 125

Glu Asp Pro Leu Thr Asn Leu Asp Lys Thr Leu Ile Met Tyr Asn Asp
130                 135                 140

Gly Ser Val Glu Ser Ile Ser Pro Asp Glu Phe Gly Lys Asn Ile Arg
145                 150                 155                 160

Ile Ala Phe Glu Lys Leu Cys His Asp Ala Trp Glu Val Phe Pro Arg
                165                 170                 175

Pro His Glu Pro Met Phe Thr Glu Arg Ala Arg Glu Leu Asp Lys Ser
            180                 185                 190

Ser Val Leu Asp Arg Ile Lys Thr Leu Gly Leu Ser Arg Leu Gln Gln
        195                 200                 205

Ala Gln Ile Asn Ser Tyr Met Ala Leu Tyr Ala Gly Glu Thr Thr Asp
    210                 215                 220

Lys Phe Gly Leu Pro Gly Val Leu Lys Leu Phe Ala Cys Gly Gly Trp
225                 230                 235                 240

Asn Tyr Asp Ala Phe Met Asp Thr Glu Thr His Tyr Arg Ile Gln Gly
                245                 250                 255

Gly Thr Ile Gly Leu Ile Asn Ala Met Leu Thr Asp Ser Gly Ala Glu
            260                 265                 270

Val Arg Met Ser Val Pro Val Thr Ala Val Glu Gln Val Asn Gly Gly
        275                 280                 285

Val Lys Ile Lys Thr Asp Asp Glu Ile Ile Thr Ala Gly Val Val
    290                 295                 300

Val Met Thr Val Pro Leu Asn Thr Tyr Lys His Ile Gly Phe Thr Pro
305                 310                 315                 320

Ala Leu Ser Lys Gly Lys Gln Arg Phe Ile Lys Glu Gly Gln Leu Ser

```
                325                 330                 335
Lys Gly Ala Lys Leu Tyr Val His Val Lys Gln Asn Leu Gly Arg Val
            340                 345                 350

Val Ala Val Ala Asp Glu Gln Gln Pro Leu Asn Val Val Gln Thr His
        355                 360                 365

Asp Tyr Ser Asp Glu Leu Gly Thr Ile Leu Ser Ile Thr Ile Ala Arg
370                 375                 380

Lys Glu Thr Ile Asp Val Asn Asp Arg Asp Ala Val Thr Arg Glu Val
385                 390                 395                 400

Gln Lys Met Phe Pro Gly Val Glu Val Leu Gly Thr Ala Ala Tyr Asp
                405                 410                 415

Trp Thr Ala Asp Pro Phe Ser Leu Gly Ala Trp Ala Ala Tyr Gly Val
            420                 425                 430

Gly Gln Leu Ser Arg Leu Lys Asp Leu Gln Ala Ala Glu Gly Arg Ile
        435                 440                 445

Leu Phe Ala Gly Ala Glu Thr Ser Asn Gly Trp His Ala Asn Ile Asp
450                 455                 460

Gly Ala Val Glu Ser Gly Leu Arg Ala Gly Arg Glu Val Lys Gln Leu
465                 470                 475                 480

Leu Ser

<210> SEQ ID NO 9
<211> LENGTH: 482
<212> TYPE: PRT
<213> ORGANISM: Pseudomonas putida S16

<400> SEQUENCE: 9

Met Ser Asp Lys Thr Lys Thr Asn Glu Gly Phe Ser Arg Arg Ser Phe
1               5                   10                  15

Ile Gly Ser Ala Ala Val Val Thr Ala Gly Val Ala Gly Leu Gly Ala
            20                  25                  30

Ile Asp Ala Ala Ser Ala Thr Gln Lys Thr Asn Arg Ala Ser Thr Val
        35                  40                  45

Lys Gly Gly Phe Asp Tyr Asp Val Val Val Gly Gly Gly Phe Ala
50                  55                  60

Gly Ala Thr Ala Ala Arg Glu Cys Gly Leu Gln Gly Tyr Arg Thr Leu
65                  70                  75                  80

Leu Leu Glu Ala Arg Ser Arg Leu Gly Gly Arg Thr Phe Thr Ser Arg
                85                  90                  95

Phe Ala Gly Gln Glu Ile Glu Phe Gly Gly Ala Trp Val His Trp Leu
            100                 105                 110

Gln Pro His Val Trp Ala Glu Met Gln Arg Tyr Gly Leu Gly Val Val
        115                 120                 125

Glu Asp Pro Leu Thr Asn Leu Asp Lys Thr Leu Ile Met Tyr Asn Asp
130                 135                 140

Gly Ser Val Glu Ser Ile Ser Pro Asp Glu Phe Gly Lys Asn Ile Arg
145                 150                 155                 160

Ile Ala Phe Glu Lys Leu Cys His Asp Ala Trp Glu Val Phe Pro Arg
                165                 170                 175

Pro His Glu Pro Met Phe Thr Glu Arg Ala Arg Glu Leu Asp Lys Ser
            180                 185                 190

Ser Val Leu Asp Arg Ile Lys Thr Leu Gly Leu Ser Arg Leu Gln Gln
        195                 200                 205

Ala Gln Ile Asn Ser Tyr Met Ala Leu Tyr Ala Gly Glu Thr Thr Asp
```

```
            210                 215                 220
Lys Phe Gly Leu Pro Gly Val Leu Lys Leu Phe Ala Cys Gly Trp
225                 230                 235                 240

Asn Tyr Asp Ala Phe Met Asp Thr Glu Thr His Tyr Arg Ile Gln Gly
                245                 250                 255

Gly Thr Ile Gly Leu Ile Asn Ala Met Leu Thr Asp Ser Gly Ala Glu
            260                 265                 270

Val Arg Met Ser Val Pro Val Thr Ala Val Glu Gln Val Asn Gly Gly
            275                 280                 285

Val Lys Ile Lys Thr Asp Asp Glu Ile Ile Thr Ala Gly Val Val
            290                 295                 300

Val Met Thr Val Pro Leu Asn Thr Tyr Lys His Ile Gly Phe Thr Pro
305                 310                 315                 320

Ala Leu Ser Lys Gly Lys Gln Arg Phe Ile Lys Glu Gly Gln Leu Ser
                325                 330                 335

Lys Gly Ala Lys Leu Tyr Val His Val Lys Gln Asn Leu Gly Arg Val
                340                 345                 350

Ala Ala Ala Ala Asp Glu Gln Gln Pro Leu Asn Ala Val Gln Thr His
                355                 360                 365

Asp Tyr Ser Asp Glu Leu Gly Thr Ile Leu Ser Ile Thr Ile Ala Arg
                370                 375                 380

Lys Glu Thr Ile Asp Val Asn Asp Arg Asp Ala Val Thr Arg Glu Val
385                 390                 395                 400

Gln Lys Met Phe Pro Gly Val Glu Val Leu Gly Thr Ala Ala Tyr Asp
                405                 410                 415

Trp Thr Ala Asp Pro Phe Ser Leu Gly Ala Trp Ala Ala Tyr Gly Val
                420                 425                 430

Gly Gln Leu Ser Arg Leu Lys Asp Leu Gln Ala Ala Glu Gly Arg Ile
                435                 440                 445

Leu Phe Ala Gly Ala Glu Thr Ser Asn Gly Trp His Ala Asn Ile Asp
                450                 455                 460

Gly Ala Val Glu Ser Gly Leu Arg Ala Gly Arg Glu Val Lys Gln Leu
465                 470                 475                 480

Leu Ser

<210> SEQ ID NO 10
<211> LENGTH: 482
<212> TYPE: PRT
<213> ORGANISM: Pseudomonas putida S16

<400> SEQUENCE: 10

Met Ser Asp Lys Thr Lys Thr Asn Glu Gly Phe Ser Arg Arg Ser Phe
1               5                   10                  15

Ile Gly Ser Ala Ala Val Val Thr Ala Gly Val Ala Gly Leu Gly Ala
                20                  25                  30

Ile Asp Ala Ala Ser Ala Thr Gln Lys Thr Asn Arg Ala Ser Thr Val
            35                  40                  45

Lys Gly Gly Phe Asp Tyr Asp Val Val Val Gly Gly Phe Ala
        50                  55                  60

Gly Ala Thr Ala Ala Arg Glu Cys Gly Leu Gly Tyr Arg Thr Leu
65                  70                  75                  80

Leu Leu Glu Ala Arg Ser Arg Leu Gly Gly Arg Thr Phe Thr Ser Arg
                85                  90                  95

Phe Ala Gly Gln Glu Ile Glu Phe Gly Gly Ala Trp Val His Trp Leu
```

```
            100                 105                 110
    Gln Pro His Val Trp Ala Glu Met Gln Arg Tyr Gly Leu Gly Val Val
            115                 120                 125

Glu Asp Pro Leu Thr Asn Leu Asp Lys Thr Leu Ile Met Tyr Asn Asp
        130                 135                 140

Gly Ser Val Glu Ser Ile Ser Pro Asp Glu Phe Gly Lys Asn Ile Arg
145                 150                 155                 160

Ile Ala Phe Glu Lys Leu Cys His Asp Ala Trp Glu Val Phe Pro Arg
                    165                 170                 175

Pro His Glu Pro Met Phe Thr Glu Arg Ala Arg Glu Leu Asp Lys Ser
                        180                 185                 190

Ser Val Leu Asp Arg Ile Lys Thr Leu Gly Leu Ser Arg Leu Gln Gln
                195                 200                 205

Ala Gln Ile Asn Ser Ala Met Ala Leu Ala Ala Gly Glu Thr Thr Asp
            210                 215                 220

Lys Phe Gly Leu Pro Gly Val Leu Lys Leu Phe Ala Cys Gly Gly Trp
225                 230                 235                 240

Asn Tyr Asp Ala Phe Met Asp Thr Glu Thr His Tyr Arg Ile Gln Gly
                    245                 250                 255

Gly Thr Ile Gly Leu Ile Asn Ala Met Leu Thr Asp Ser Gly Ala Glu
                        260                 265                 270

Val Arg Met Ser Val Pro Val Thr Ala Val Glu Gln Val Asn Gly Gly
                275                 280                 285

Val Lys Ile Lys Thr Asp Asp Glu Ile Ile Thr Ala Gly Val Val
            290                 295                 300

Val Met Thr Val Pro Leu Asn Thr Tyr Lys His Ile Gly Phe Thr Pro
305                 310                 315                 320

Ala Leu Ser Lys Gly Lys Gln Arg Phe Ile Lys Glu Gly Gln Leu Ser
                    325                 330                 335

Lys Gly Ala Lys Leu Tyr Val His Val Lys Gln Asn Leu Gly Arg Val
                        340                 345                 350

Val Ala Val Ala Asp Glu Gln Gln Pro Leu Asn Val Val Gln Thr His
                355                 360                 365

Asp Tyr Ser Asp Glu Leu Gly Thr Ile Leu Ser Ile Thr Ile Ala Arg
            370                 375                 380

Lys Glu Thr Ile Asp Val Asn Asp Arg Asp Ala Val Thr Arg Glu Val
385                 390                 395                 400

Gln Lys Met Phe Pro Gly Val Glu Val Leu Gly Thr Ala Ala Tyr Asp
                    405                 410                 415

Trp Thr Ala Asp Pro Phe Ser Leu Gly Ala Trp Ala Ala Tyr Gly Val
                        420                 425                 430

Gly Gln Leu Ser Arg Leu Lys Asp Leu Gln Ala Ala Glu Gly Arg Ile
                435                 440                 445

Leu Phe Ala Gly Ala Glu Thr Ser Asn Gly Trp His Ala Asn Ile Asp
            450                 455                 460

Gly Ala Val Glu Ser Gly Leu Arg Ala Gly Arg Glu Val Lys Gln Leu
465                 470                 475                 480

Leu Ser

<210> SEQ ID NO 11
<211> LENGTH: 482
<212> TYPE: PRT
<213> ORGANISM: Pseudomonas putida S16
```

```
<400> SEQUENCE: 11

Met Ser Asp Lys Thr Lys Thr Asn Glu Gly Phe Ser Arg Arg Ser Phe
1               5                   10                  15

Ile Gly Ser Ala Ala Val Val Thr Ala Gly Val Ala Gly Leu Gly Ala
            20                  25                  30

Ile Asp Ala Ala Ser Ala Thr Gln Lys Thr Asn Arg Ala Ser Thr Val
        35                  40                  45

Lys Gly Gly Phe Asp Tyr Asp Val Val Val Gly Gly Gly Phe Ala
    50                  55                  60

Gly Ala Thr Ala Ala Arg Glu Cys Gly Leu Gln Gly Tyr Arg Thr Leu
65                  70                  75                  80

Leu Leu Glu Ala Arg Ser Arg Leu Gly Gly Arg Thr Phe Thr Ser Arg
                85                  90                  95

Phe Ala Gly Gln Glu Ile Glu Phe Gly Gly Ala Trp Val His Trp Leu
                100                 105                 110

Gln Pro His Val Trp Ala Glu Met Gln Arg Tyr Gly Leu Gly Val Val
            115                 120                 125

Glu Asp Pro Leu Thr Asn Leu Asp Lys Thr Leu Ile Met Tyr Asn Asp
130                 135                 140

Gly Ser Val Glu Ser Ile Ser Pro Asp Glu Phe Gly Lys Asn Ile Arg
145                 150                 155                 160

Ile Ala Ala Glu Lys Leu Cys His Asp Ala Trp Glu Val Phe Pro Arg
                165                 170                 175

Pro His Glu Pro Met Phe Thr Glu Arg Ala Arg Glu Leu Asp Lys Ser
            180                 185                 190

Ser Val Leu Asp Arg Ile Lys Thr Leu Gly Leu Ser Arg Leu Gln Gln
        195                 200                 205

Ala Gln Ile Asn Ser Ala Met Ala Leu Ala Ala Gly Glu Thr Thr Asp
210                 215                 220

Lys Phe Gly Leu Pro Gly Val Leu Lys Leu Phe Ala Cys Gly Gly Trp
225                 230                 235                 240

Asn Tyr Asp Ala Phe Met Asp Thr Ala Thr His Tyr Arg Ile Gln Gly
                245                 250                 255

Gly Thr Ile Gly Leu Ile Asn Ala Met Leu Thr Asp Ser Gly Ala Glu
            260                 265                 270

Val Arg Met Ser Val Pro Val Thr Ala Val Glu Gln Val Asn Gly Gly
        275                 280                 285

Val Lys Ile Lys Thr Asp Asp Glu Ile Ile Thr Ala Gly Val Val
    290                 295                 300

Val Met Thr Val Pro Leu Asn Thr Tyr Lys His Ile Gly Phe Thr Pro
305                 310                 315                 320

Ala Leu Ser Lys Gly Lys Gln Arg Phe Ile Lys Glu Gly Gln Leu Ser
                325                 330                 335

Lys Gly Ala Lys Leu Tyr Val His Val Lys Gln Asn Leu Gly Arg Val
            340                 345                 350

Val Ala Val Ala Asp Glu Gln Gln Pro Leu Asn Val Gln Thr His
        355                 360                 365

Asp Tyr Ser Asp Glu Leu Gly Thr Ile Leu Ser Ile Thr Ile Ala Arg
370                 375                 380

Lys Glu Thr Ile Asp Val Asn Asp Arg Asp Ala Val Thr Arg Glu Val
385                 390                 395                 400

Gln Lys Met Phe Pro Gly Val Glu Val Leu Gly Thr Ala Ala Tyr Asp
                405                 410                 415
```

```
Trp Thr Ala Asp Pro Phe Ser Leu Gly Ala Trp Ala Ala Tyr Gly Val
            420                 425                 430

Gly Gln Leu Ser Arg Leu Lys Asp Leu Gln Ala Ala Glu Gly Arg Ile
        435                 440                 445

Leu Phe Ala Gly Ala Glu Thr Ser Asn Gly Trp His Ala Asn Ile Asp
450                 455                 460

Gly Ala Val Glu Ser Gly Leu Arg Ala Gly Arg Glu Val Lys Gln Leu
465                 470                 475                 480

Leu Ser

<210> SEQ ID NO 12
<211> LENGTH: 425
<212> TYPE: PRT
<213> ORGANISM: Arthrobacter nicotinovorans

<400> SEQUENCE: 12

Met Tyr Asp Ala Ile Val Val Gly Gly Phe Ser Gly Leu Lys Ala
1               5                   10                  15

Ala Arg Asp Leu Thr Asn Ala Gly Lys Lys Val Leu Leu Glu Gly
            20                  25                  30

Gly Glu Arg Leu Gly Gly Arg Ala Tyr Ser Arg Glu Ser Arg Asn Val
        35                  40                  45

Pro Gly Leu Arg Val Glu Ile Gly Gly Ala Tyr Leu His Arg Lys His
    50                  55                  60

His Pro Arg Leu Ala Ala Glu Leu Asp Arg Tyr Gly Ile Pro Thr Ala
65                  70                  75                  80

Ala Ala Ser Glu Phe Thr Ser Phe Arg His Arg Leu Gly Pro Thr Ala
                85                  90                  95

Val Asp Gln Ala Phe Pro Ile Pro Gly Ser Glu Ala Val Ala Val Glu
            100                 105                 110

Ala Ala Thr Tyr Thr Leu Leu Arg Asp Ala His Arg Ile Asp Leu Glu
        115                 120                 125

Lys Gly Leu Glu Asn Gln Asp Leu Glu Asp Leu Asp Ile Pro Leu Asn
130                 135                 140

Glu Tyr Val Asp Lys Leu Asp Leu Pro Pro Val Ser Arg Gln Phe Leu
145                 150                 155                 160

Leu Ala Trp Ala Trp Asn Met Leu Gly Gln Pro Ala Asp Gln Ala Ser
                165                 170                 175

Ala Leu Trp Met Leu Gln Leu Val Ala Ala His His Tyr Ser Ile Leu
            180                 185                 190

Gly Val Val Leu Ser Leu Asp Glu Val Phe Ser Asn Gly Ser Ala Asp
        195                 200                 205

Leu Val Asp Ala Met Ser Gln Glu Ile Pro Glu Ile Arg Leu Gln Thr
210                 215                 220

Val Val Thr Gly Ile Asp Gln Ser Gly Asp Val Val Asn Val Thr Val
225                 230                 235                 240

Lys Asp Gly His Ala Phe Gln Ala His Ser Val Ile Val Ala Thr Pro
                245                 250                 255

Met Asn Thr Trp Arg Arg Ile Val Phe Thr Pro Ala Leu Pro Glu Arg
            260                 265                 270

Arg Arg Ser Val Ile Glu Glu Gly His Gly Gly Gln Gly Leu Lys Ile
        275                 280                 285

Leu Ile His Val Arg Gly Ala Glu Ala Gly Ile Glu Cys Val Gly Asp
290                 295                 300
```

```
Gly Ile Phe Pro Thr Leu Tyr Asp Tyr Cys Glu Val Ser Glu Ser Glu
305                 310                 315                 320

Arg Leu Leu Val Ala Phe Thr Asp Ser Gly Ser Phe Asp Pro Thr Asp
                325                 330                 335

Ile Gly Ala Val Lys Asp Ala Val Leu Tyr Tyr Leu Pro Glu Val Glu
                340                 345                 350

Val Leu Gly Ile Asp Tyr His Asp Trp Ile Ala Asp Pro Leu Phe Glu
                355                 360                 365

Gly Pro Trp Val Ala Pro Arg Val Gly Gln Phe Ser Arg Val His Lys
                370                 375                 380

Glu Leu Gly Glu Pro Ala Gly Arg Ile His Phe Val Gly Ser Asp Val
385                 390                 395                 400

Ser Leu Glu Phe Pro Gly Tyr Ile Glu Gly Ala Leu Glu Thr Ala Glu
                405                 410                 415

Cys Ala Val Asn Ala Ile Leu His Ser
                420                 425

<210> SEQ ID NO 13
<211> LENGTH: 478
<212> TYPE: PRT
<213> ORGANISM: Pseudomonas sp.

<400> SEQUENCE: 13

Met Asp Glu Lys Arg Asn Asn Gly Leu Ser Arg Arg Ser Phe Ile Gly
1               5                   10                  15

Gly Ala Ala Val Val Thr Ala Gly Ala Ala Gly Leu Gly Leu Ile Gly
                20                  25                  30

Ser Ala Asn Ala Thr Glu Asn Gly Thr Ser Lys Arg Ala Thr Gly Phe
                35                  40                  45

Asp Tyr Asp Val Ile Val Gly Gly Phe Ala Gly Ala Thr Ala
            50                  55                  60

Ala Arg Glu Cys Gly His Gln Gly Tyr Lys Thr Leu Leu Leu Glu Ala
65                  70                  75                  80

Arg Ser Arg Leu Gly Gly Arg Thr Phe Thr Ser His Phe Ala Gly Gln
                85                  90                  95

Glu Ile Glu Phe Gly Gly Ala Trp Val His Trp Leu Gln Pro His Val
                100                 105                 110

Trp Ser Glu Met Gln Arg Tyr Gly Leu Gly Val Val Glu Asp Pro Leu
                115                 120                 125

Thr Asn Leu Asp Lys Thr Leu Val Met Tyr Asn Asp Gly Ser Val Glu
                130                 135                 140

Asp Leu Pro Pro Glu Val Phe Gly Thr Asn Ile Gln Val Ala Phe Glu
145                 150                 155                 160

Lys Met Cys His Asp Ala Trp Glu Ala Phe Pro Arg Pro His Glu Pro
                165                 170                 175

Met Phe Thr Glu Arg Ala Arg Lys Leu Asp Lys Met Ser Val Leu Asp
                180                 185                 190

Arg Ile Asn Gln Leu Glu Leu Thr Arg Ala Gln Arg Ala Glu Leu Asn
                195                 200                 205

Ser Tyr Met Ala Leu Tyr Gly Gly Glu Thr Thr Asp Lys Tyr Gly Leu
                210                 215                 220

Pro Gly Val Leu Lys Leu Phe Ala Cys Gly Gly Trp Asn Tyr Asn Ala
225                 230                 235                 240

Phe Met Asp Thr Glu Thr His Tyr Arg Ile Glu Gly Gly Thr Ile Gly
```

```
                245                 250                 255
Leu Ile Asn Ala Met Leu Ala Asp Ser Gly Ala Glu Val Arg Leu Asn
            260                 265                 270

Met Pro Val Ile Ser Val Glu Gln Leu Asn Gly Gly Val Arg Val Glu
        275                 280                 285

Thr Asp Gly Glu Thr Ile Thr Ala Gly Thr Ile Ile Met Thr Val
    290                 295                 300

Pro Leu Asn Thr Tyr Arg His Ile Asn Phe Thr Pro Ala Leu Ser Glu
305                 310                 315                 320

Gly Lys Gln Arg Phe Ile Gln Glu Gly Gln Leu Ser Lys Gly Ala Lys
                325                 330                 335

Leu Tyr Val His Val Lys Glu Asn Leu Gly Arg Val Phe Ala Phe Ala
            340                 345                 350

Asp Glu Gln Gln Pro Leu Asn Trp Val Gln Thr His Asp Tyr Gly Asp
        355                 360                 365

Glu Leu Gly Thr Ile Leu Ser Ile Thr Ile Ala Arg Ala Glu Thr Ile
    370                 375                 380

Asp Val Asn Asp Arg Asp Ala Val Thr Arg Glu Ile Arg Lys Leu Phe
385                 390                 395                 400

Pro Gly Val Glu Val Leu Gly Ile Ala Ala Tyr Asp Trp Thr Ala Asp
                405                 410                 415

Pro Phe Ser Leu Gly Ala Trp Ala Ala Tyr Gly Val Gly Gln Leu Ser
            420                 425                 430

Arg Leu Thr Asp Leu Gln Gln Pro Glu Gly Arg Ile Leu Phe Ala Gly
        435                 440                 445

Ala Glu Thr Ser Asn Gly Trp His Ala Asn Ile Asp Gly Ala Val Glu
    450                 455                 460

Ser Gly Leu Arg Ala Gly Arg Glu Ala Lys Glu Ile Leu Gly
465                 470                 475

<210> SEQ ID NO 14
<211> LENGTH: 485
<212> TYPE: PRT
<213> ORGANISM: Pseudomonas sp.

<400> SEQUENCE: 14

Met Ala Glu His Glu Asn Gly Ala Gln Gly Val Ser Arg Arg Lys Phe
1               5                   10                  15

Leu His Gly Ala Gly Val Gly Ala Val Ala Val Ala Gly Ala Gly Val
            20                  25                  30

Met Thr Arg Ala Thr Ala Ala Ser Gly Asp Asn Cys Lys Thr Ala Gly
        35                  40                  45

Cys Asp Tyr Asp Val Val Ile Gly Gly Phe Ala Gly Val Thr
    50                  55                  60

Ala Ala Arg Asp Ser Arg Lys Asn Gly Tyr Lys Thr Leu Leu Leu Glu
65                  70                  75                  80

Ala Arg Asn Arg Leu Gly Gly Arg Thr Phe Thr Ser Glu Phe Asp Gly
                85                  90                  95

His Lys Val Glu Met Gly Gly Thr Trp Ile His Gln Ala Gln Pro Phe
            100                 105                 110

Val Trp Ala Glu Lys Glu Arg Tyr Gly Leu Glu Val Leu Glu Thr Pro
        115                 120                 125

Val Ser Gly Val Ala Leu Asp Lys Glu Glu Tyr Val Val Lys Val Gly
    130                 135                 140
```

```
Asp Thr Thr His Thr Leu Ser Gly Glu Gln Leu Pro Leu Tyr Glu
145                 150                 155                 160

Ala Leu Asp Ala Phe Tyr Val Glu Ala Arg Gln Val Trp Asp Arg Pro
            165                 170                 175

Tyr Asp Ala Gln Tyr Thr Trp Asn Glu Ile Ile Arg Arg Asp Lys Arg
            180                 185                 190

Thr Gly Gln Gln Arg Leu Asp Glu Leu Lys Leu Asn Pro Val Gln Arg
        195                 200                 205

Val Ala Ile Asp Ser Phe Val Gly Ala Thr Ala Ala Pro Leu Asp
    210                 215                 220

Gln Thr Ser Tyr Val Asp Met Leu Arg Tyr Trp Ala Leu Ser Gly Trp
225                 230                 235                 240

Asn Leu Gln Gly Phe Asn Asp Ala Val Val Arg Tyr Lys Leu Lys Asp
            245                 250                 255

Gly Thr Val Gly Leu Ile Asn Lys Met Ile Glu Asp Gly Lys Pro Gln
        260                 265                 270

Val Arg Leu Ser Thr Pro Val Lys Lys Ile Glu Asp Lys Gly Asp His
    275                 280                 285

Thr Val Val Thr Thr Gln Lys Gly Glu Lys Ile Val Ala Ala Ser Val
290                 295                 300

Ile Ile Ala Leu Pro Met Asn Val Leu Pro Asn Leu Glu Phe Ser Pro
305                 310                 315                 320

Ala Leu Asp Pro Val Leu Ile Glu Ala Gly Lys Gln Lys His Ser Gly
            325                 330                 335

Lys Gly Ile Lys Phe Tyr Ile Lys Ala Arg Gly Gly Phe Thr Lys Leu
        340                 345                 350

Ala Lys Val Thr Ala Met Ala Asp Ser Asn Tyr Pro Val Asn Leu Val
    355                 360                 365

Met Ala His Tyr Val Ser Asp Asp Tyr Thr Leu Phe Val Ala Phe Gly
370                 375                 380

Asn Asp Pro Gly Lys Ile Asp Ile Phe Asp Ile Lys Ala Val Gln Ser
385                 390                 395                 400

Ile Leu Glu Pro Leu Phe Pro Gly Ile Gln Val Glu Ser Thr His Gly
            405                 410                 415

Tyr Glu Trp Thr Leu Asp Pro Tyr Ser Leu Gly Thr Tyr Ala Ser Tyr
        420                 425                 430

Lys Pro Glu Trp Phe Glu Lys Tyr Tyr Ala His Phe Gln Lys Asp Ser
    435                 440                 445

Gly Arg Ile Phe Phe Gly Gln Gly Asp His Gly Glu Gly Trp Arg Gly
450                 455                 460

Cys Ile Asp Gly Ala Ile Ala Ala Gly Gly Lys Ala Ala Gln Arg Thr
465                 470                 475                 480

Lys Glu Leu Leu Gly
            485

<210> SEQ ID NO 15
<211> LENGTH: 443
<212> TYPE: PRT
<213> ORGANISM: Rhodococcus wratislaviensis

<400> SEQUENCE: 15

Met Gly Asn Asn Gln Ser Cys Asp Val Val Ile Gly Ala Gly Phe
1               5                   10                  15

Ala Gly Ile Thr Ala Ser Arg Glu Leu Ser Arg Arg Gly Tyr Asp Val
            20                  25                  30
```

```
Val Val Leu Glu Gly Arg Asp Arg Ile Gly Gly Arg Thr Trp Tyr Lys
        35                  40                  45

Asp Asp Ala Leu Pro Gly His Ser Leu Glu Leu Gly Gly Thr Trp Val
50                  55                  60

His Trp Phe Gln Pro His Ala Phe Ala Glu Ile Ser Arg Tyr Asn Leu
65                  70                  75                  80

Glu Leu Val Glu Thr Ile Gly Val Ser Ala Pro Glu Ile Ala Ala Thr
                85                  90                  95

Val Thr Gly Gly Arg Arg Lys Ser Val Pro Tyr Glu Ala Ser Ser
                100                 105                 110

Ala Ile Glu Ser Leu Met Glu Met Val Val Gln Asp Ala Arg Glu Val
                115                 120                 125

Leu Glu Arg Pro Phe Glu Pro Phe Phe His Lys Asp Ala Leu Glu Val
            130                 135                 140

Ile Asp Lys Leu Ser Ile Gln Asp Arg Ile Asp Gly Leu Asp Leu Thr
145                 150                 155                 160

Pro Glu Glu Lys Asp Leu Ala Asn Gly Leu Trp Thr Ala Met Gly Ser
                    165                 170                 175

Ala Pro Cys Gly Asp Val Gly Leu Val Ala Ala Leu Arg Trp Tyr Ala
                180                 185                 190

Leu Ser Gly Phe Asp Ile Asn Ala Val Phe Asp Thr Val Gly Arg Tyr
            195                 200                 205

Lys Leu Lys Asn Gly Thr Arg Ser Leu Ile Gln Ala Ile Ala Asp Asp
    210                 215                 220

Ser Ser Ala Glu Ile Arg Leu Ser Thr Pro Val Ala Ala Val Glu Gln
225                 230                 235                 240

Ser Asp Asp Gly Val Val Thr Thr Arg Gln Gly Asp Thr Leu Arg
                245                 250                 255

Ala Arg Tyr Val Val Val Ala Ala Pro Leu Asn Thr Phe Gly Ala Ile
                260                 265                 270

Asp Phe Ser Pro Pro Leu Ser Ala Ala Lys Gln Ala Gly Ile Ser Glu
        275                 280                 285

Gly Gln Pro Gly Arg Gly Ser Lys Ala Trp Val His Val Arg Gly Asp
    290                 295                 300

Leu Pro Lys Pro Phe Phe Ala Val Ala Pro Glu Asn His Leu Ile Asn
305                 310                 315                 320

Tyr Val Val Thr Asp Lys Val Leu Asp Asp Gly Gln Leu Leu Ile Ala
                325                 330                 335

Phe Gly Pro Glu Gly Ala Asp Leu Asn Ala Gly Asp Ile Asp Gln Val
            340                 345                 350

Gly Ala Glu Leu Gln Lys Leu Phe Gly Asp Leu Glu Val Val Ala Thr
        355                 360                 365

Thr Gly His Asp Trp Ala Ser Asp Glu Phe Ser Arg Gly Thr Trp Cys
    370                 375                 380

Met Phe Arg Pro Gly Gln Thr Thr Arg Leu Leu Ala Glu Leu Gln Lys
385                 390                 395                 400

Pro Glu Gly Arg Val Phe Phe Ala Gly Ser Asp Leu Ala Asn Gly Trp
                405                 410                 415

Asn Gly Phe Ile Asp Gly Ala Ile Glu Ser Gly Ile Arg Ala Asp Arg
            420                 425                 430

Glu Ile His Ala Arg Ile Ser Gly Asn Pro Ser
    435                 440
```

<210> SEQ ID NO 16
<211> LENGTH: 428
<212> TYPE: PRT
<213> ORGANISM: Conexibacter woesei

<400> SEQUENCE: 16

Thr Ser Cys Asp Ala Ile Val Val Gly Gly Phe Ala Gly Val Thr
1               5                   10                  15

Ala Ala Arg Glu Leu Ser Asn Ala Gly Leu Ser Thr Thr Leu Leu Glu
            20                  25                  30

Ala Arg Asp Arg Leu Gly Gly Arg Thr Trp Thr Ser Gln Phe Gly Ser
            35                  40                  45

Arg Thr Val Glu Leu Gly Gly Gly Trp Val His Trp Arg Gln Pro His
50                  55                  60

Val Trp Ala Glu Met Thr Arg Ser Gly Ile Gly Ile Ala Glu Asp Asp
65                  70                  75                  80

Trp Arg Phe Asp Thr Ala Leu Phe Gly Ala Pro Val Gln Arg His Pro
                85                  90                  95

Pro Glu Glu Ala Phe Ala Arg Val Arg Glu Leu Phe Thr Arg Phe Ala
                100                 105                 110

Gly Asp Ala Gly Ala Leu Leu Pro His Pro His Asp Pro Leu Arg Val
            115                 120                 125

Thr Gly Val Ala Ala Leu Asp Ala Arg Ser Met Gln Asp Arg Leu Asp
130                 135                 140

Glu Met Arg Leu Thr Gly Ser Asp Glu Glu Trp Leu Ser Gly Leu Leu
145                 150                 155                 160

Tyr Glu Ile Ala Gly Ser Pro Leu Asp Glu Ala Ala Leu Leu Gln Val
                165                 170                 175

Val Arg Trp Met Ala Leu Ser Asp Trp Asp Ile Asp Arg Trp Tyr Asp
                180                 185                 190

Thr Asn Arg Tyr Arg Pro Val Gly Gly Thr Val Ala Val Leu Asp Gly
            195                 200                 205

Ile Val Ala Ser Gly Arg Phe Asp Val Gln Leu Ser Ala Pro Val Ser
210                 215                 220

Ala Val Asp Ala Gly Arg Asp Ala Val Arg Val Thr Arg Asp Gly
225                 230                 235                 240

Arg Ala Phe Arg Ala Ser Thr Val Val Ile Ala Thr Pro Val Asn Val
                245                 250                 255

Trp Pro His Ile Asp Phe Gly Pro Gly Leu Pro Ala Ala His Arg Glu
                260                 265                 270

Ala Gly Arg Val Gly Trp Gly Lys Pro His Gln Asp Lys Val Trp Ile
            275                 280                 285

Glu Val Arg Gly Ser Leu Gly Arg Val Phe Gly Gln Leu Pro Ala Pro
290                 295                 300

Ala Pro Leu Asn Phe Phe Trp Thr His Glu Ala Trp Glu Gly Gly Gln
305                 310                 315                 320

Leu Ile Ile Gly Ile Asn Ala Asn Pro Ala Leu Asp Val Thr Asp Glu
                325                 330                 335

Glu Gln Val Ala Ala Thr Ile Arg Arg Tyr Val Pro Glu Ile Asp Glu
            340                 345                 350

Val Val Ala Val Ser Gly His Asp Trp Ala Ala Asp Glu Tyr Thr Arg
            355                 360                 365

Gly Gly Asn Thr Gly His Arg Pro Gln Gln Val Thr Arg Asn Leu His
370                 375                 380

Ala Leu Gln Gln Pro Trp Gly Arg Val Ala Phe Ala Thr Ala Asp Ile
385                 390                 395                 400

Ala Ser Gly Trp Phe Gly Tyr Ile Asp Gly Ala Ile Glu Ser Gly Ile
            405                 410                 415

Arg Ala Ala Arg Asp Cys Arg Ala Ile Leu Ala Arg
            420                 425

<210> SEQ ID NO 17
<211> LENGTH: 480
<212> TYPE: PRT
<213> ORGANISM: Thauera phenylacetica

<400> SEQUENCE: 17

Met Glu Asp Lys Thr Cys Ala Ala Ser Ala Ala Gly Ala Asp Gly Ser
1               5                   10                  15

Ala Arg Arg Arg Phe Leu Lys Leu Ala Ser Thr Ala Ala Ala Ala Ser
            20                  25                  30

Val Leu Pro Ala Gly Ala Ala Ala Pro Ala Lys Pro Gly Tyr
        35                  40                  45

Asp Val Val Val Gly Gly Gly Phe Ala Gly Val Thr Ala Ala Arg
    50                  55                  60

Glu Leu Ala His Arg Gly Ala Arg Val Leu Leu Glu Ala Arg Asn
65                  70                  75                  80

Arg Leu Gly Gly Arg Thr Phe Tyr Ser Lys Phe Gly Glu Arg Lys Val
                85                  90                  95

Glu Leu Gly Gly Thr Trp Ile His Tyr Thr Gln Pro His Val Trp Ala
            100                 105                 110

Glu Val Met Arg Tyr Gly Met Glu Ile Ala Glu Thr Pro Gly Val Ala
            115                 120                 125

His Pro Asp Arg Val Leu Trp Met Ser Glu Gly Lys Val Leu Glu Ile
        130                 135                 140

Pro Val Met Glu Asn Trp Ala Leu Leu Glu Asp Ala Leu Lys Arg Phe
145                 150                 155                 160

His Ala Glu Ala Gly Glu Val Phe Glu Arg Pro Phe Met Ala Gly Leu
                165                 170                 175

Ser Ala Ala Gly Arg Lys Leu Asp His Leu Ser Ile Ala Asp Arg Met
            180                 185                 190

Ala Ala Met Glu Met Ser Pro Ala Gln Arg Asp Leu Met Asn Ala Met
        195                 200                 205

Met Ala Thr Asn Cys His Gly Pro Ile Ala Thr Gly Ala Tyr Thr Glu
        210                 215                 220

Met Leu Arg Trp Trp Ser Leu Val Asp Gly Asp Ala Ala Arg Leu Leu
225                 230                 235                 240

Tyr Ser Cys Ala Arg Tyr Lys Leu Lys Asp Gly Thr Ala Ala Leu Ile
                245                 250                 255

Glu Arg Met Ala Glu Asp Gly Gly Phe Asp Val Arg Leu Ser Thr Ala
            260                 265                 270

Val Ala Glu Leu Ser Gln Asp Ala Ala Gly Val Ser Leu Val Thr Glu
        275                 280                 285

Ala Asp Glu Arg Ile Ser Ala Arg Tyr Ala Val Ala Val Pro Val
        290                 295                 300

Asn Thr Ala Gly Gln Ile Glu Phe Ser Pro Pro Leu Arg Pro Gly Lys
305                 310                 315                 320

Thr Ala Met Ala Lys Glu His His Ala Gly Lys Gly His Lys Leu Tyr

```
                          325                 330                 335
Leu Lys Val Lys Gly Arg Leu Glu Thr Leu Ile Phe Phe Ala Pro Glu
                340                 345                 350

Thr Glu Leu Phe Thr Met Val Phe Thr Asp Gln Pro Gly Glu Asp Gly
                355                 360                 365

Gly Val Leu Val Ala Phe Gly Pro Pro Leu Asp Gly Lys Val Asp Leu
        370                 375                 380

Asn Asp Pro Lys Ala Val Glu Pro Phe Val Arg Arg Phe Leu Pro His
385                 390                 395                 400

Leu Ser Val Glu Gln Val Leu Gly Tyr Asp Trp Gly Leu Asp Pro Tyr
                405                 410                 415

Ser Arg Gly Thr Trp Cys Thr Leu Arg Pro Gly Gln Phe Gly Lys His
                420                 425                 430

Leu Glu Asp Leu Arg Ala Arg Glu Gly Arg Val Phe Phe Ala Gly Ala
                435                 440                 445

Asp Ile Ala Thr Gly Trp Arg Gly Phe Ile Asp Gly Ala Ile Glu Ser
        450                 455                 460

Gly Leu Gln Val Gly Gln Ala Val Ala Ala Glu Leu Arg Gly Arg Ala
465                 470                 475                 480

<210> SEQ ID NO 18
<211> LENGTH: 436
<212> TYPE: PRT
<213> ORGANISM: Saccharopolyspora erythraea

<400> SEQUENCE: 18

Met Arg Ile Asp Val Asp Ser Tyr Asp Val Ile Val Ile Gly Ala
1               5                   10                  15

Gly Phe Ala Gly Leu Thr Ala Ala Arg Glu Leu Ser Leu Arg Gly Arg
                20                  25                  30

Ser Val Val Val Leu Glu Ala Arg Asp Arg Ile Gly Gly Arg Thr Trp
            35                  40                  45

Thr Asp Val Arg Phe Gly Arg Pro Leu Glu Met Gly Gly Thr Trp Val
        50                  55                  60

His Trp Leu Gln Pro His Thr Trp Ser Glu Ile Thr Arg Tyr Gly Leu
65                  70                  75                  80

Asp Val Glu Pro Ser Pro Gly Ser Glu Glu Val Tyr Trp Ile Ala Gly
                85                  90                  95

Gly Gln Val His Lys Gly Thr Pro Ala Glu Phe Asp Ala Leu Ile Glu
            100                 105                 110

Arg Gly Met Asp Arg Leu Ala Glu Asp Ser Arg Glu Phe Phe Glu Met
            115                 120                 125

Pro Tyr Glu Pro Leu Arg His Arg Gly Leu Asp Ala Ile Asp His Glu
        130                 135                 140

Ser Val Val Asp Tyr Phe Gly Arg Leu Asp Leu Asp Pro Thr Glu Arg
145                 150                 155                 160

Glu Val Thr Thr Gly Val Trp Ala Glu His Phe Asn Ala Pro Ala Glu
                165                 170                 175

Val Ser Gly Leu Ala Gln Ala Met Arg Trp Cys Ala Ala Ala Ser Gly
            180                 185                 190

Asp Trp Arg Leu Leu His Glu Ala Thr Ser Gly Tyr Arg Leu Gly Thr
        195                 200                 205

Gly Thr Ala Ala Leu Ala Ser Ala Met Ala Glu Asp Gly Asp Ala Glu
    210                 215                 220
```

```
Phe Arg Leu Arg Thr Val Val Thr Ala Val Arg Gln Glu Asp Gly Arg
225                 230                 235                 240

Ala Thr Ala Thr Thr Ala Asp Gly Lys Arg Tyr Thr Ala Arg Arg Ile
            245                 250                 255

Val Cys Thr Leu Pro Leu Asn Val Leu Gly Ser Ile Asp Phe Gln Pro
        260                 265                 270

Gly Leu Pro Ala Ala Lys Leu Ala Ala Ser Ala Glu Arg Thr Ala Ser
    275                 280                 285

Gln Gly Leu Lys Thr Trp Ile Arg Val Arg Gly His Ile Ala Pro Phe
290                 295                 300

Thr Ala Tyr Ala Pro Asp Asp His Ala Leu Thr Phe Val Arg Pro Glu
305                 310                 315                 320

Tyr Thr Val Asp Gly Asp Thr Val Leu Val Ala Phe Gly Thr Arg Ala
            325                 330                 335

Ser Asp Leu Asp Pro Thr Asp Ala Asp Gly Val Ala Arg Ala Leu Arg
        340                 345                 350

Cys Trp Arg Asp Asp Leu Glu Val Val Asp Val Thr Gly His Asp Trp
    355                 360                 365

Met Arg Asp Thr Phe Ser Arg Glu Thr Trp Pro Met Gln Arg Pro Gly
370                 375                 380

Gln Leu Thr Arg Tyr Leu Ala Ala Leu Arg Glu Pro His Gly Gly Val
385                 390                 395                 400

His Phe Ala Gly Ser Asp Ile Ala Gly Gly Trp Ala Gly Phe Ile Asp
            405                 410                 415

Gly Ala Ile Glu Ser Gly Leu His Ala Ala Arg His Val Glu Thr Ala
        420                 425                 430

Leu Arg Thr Gly
        435

<210> SEQ ID NO 19
<211> LENGTH: 450
<212> TYPE: PRT
<213> ORGANISM: Herbaspirillum seropedicae

<400> SEQUENCE: 19

Met His Gly Leu Pro Ser Pro Ala Ala Leu Ser Ser Lys Ile Pro Asp
1               5                   10                  15

Gly Asn Ala Tyr Asp Val Val Val Gly Ala Gly Phe Ala Gly Leu
            20                  25                  30

Thr Ala Ala Arg Glu Leu Gly Ser Arg Gly Leu Arg Val Ala Ile Val
            35                  40                  45

Glu Ala Arg Asp Arg Ile Gly Gly Arg Thr Phe Ile Ala Glu Gln Asn
    50                  55                  60

Gly Gln Lys Tyr Glu Val Gly Gly Thr Trp Val His Trp Gly Gln Ala
65                  70                  75                  80

Tyr Val Trp Asn Glu Leu His Arg Tyr Gly Leu Gly Ile Ser Glu Ser
                85                  90                  95

Ile Ser Gly Thr Pro Glu Ser Ile Ser Leu Leu Thr Ser Gln Gly Leu
            100                 105                 110

Glu Thr Asp Ser Ala Glu Ala Met Gly Lys Asp Leu Ser Ala Ala Leu
        115                 120                 125

Gln Leu Phe Cys Asp Val Asp Gly Ala Arg Gly Glu Ile Ala Phe Ala
    130                 135                 140

Asn Pro His Cys Pro Asp Pro Val Ala Asp Arg Phe Asp Ser Ile Ser
145                 150                 155                 160
```

Leu Ala Glu Arg Leu Ala Gln Ile Glu Leu Ser Ser Arg Gln Arg Ala
165                 170                 175

Leu Leu Glu Ala Phe Val Thr Met Asn Ala Ala Thr Asp Pro Ala Lys
            180                 185                 190

Gly Gly Phe Tyr Asp Gln Leu Arg Trp Trp Ala Leu Gly Glu Tyr Ser
        195                 200                 205

Thr Glu Ala Leu Leu Lys Arg Leu Gly Arg Tyr Lys Ile Ala Lys Gly
    210                 215                 220

Thr Ser Ala Leu Ala Leu Ala Leu Leu Lys Asp Ser Lys Ala Asp Leu
225                 230                 235                 240

Phe Val Gly Glu Pro Val Ser Glu Ile Thr Ala Arg Ala Asp Gly Val
                245                 250                 255

Arg Leu Gln Ala Arg Asn Ile Ser Leu Gln Ala Lys Ser Leu Val Val
            260                 265                 270

Ala Val Pro Met Asn Val Leu Gly Asp Ile Arg Phe Thr Ser Gly Leu
        275                 280                 285

Pro Gln Ala Arg Glu Gln Ala His Arg Gln Arg His Val Cys Ala Gly
    290                 295                 300

Thr Lys Phe Ile Ala Gln Val Asp Arg Asn Val Gly Ala Trp Ile Gly
305                 310                 315                 320

Phe Ala Pro Tyr Pro Asn Ala Leu Thr Met Val Ile Ser Asp Arg Val
                325                 330                 335

Ile Asn Gly Lys Ser Leu Leu Val Gly Phe Gly Pro Asp Asp Lys Ile
            340                 345                 350

Asp Leu Thr Asp Ile Gly Gln Ile Gln Ser Glu Leu Arg Lys Phe Leu
        355                 360                 365

Pro Asp Ile Asn Val Thr Glu Val Leu Ala His Asp Trp Ile Asn Asp
    370                 375                 380

Pro Tyr Ala Lys Gly Gly Trp Thr Trp Phe Ala Pro Asn Gln Thr Thr
385                 390                 395                 400

Arg His Leu Ala Ser Leu Gln Ala Ser Ala Pro Pro Leu Phe Phe Ala
                405                 410                 415

Asn Thr Asp Trp Ala Ser Gly Trp Arg Gly Phe Ile Asp Gly Ala Ile
            420                 425                 430

Glu Glu Gly Ile Arg Ala Ala Arg Glu Val Gly Glu Phe Leu Ser Pro
        435                 440                 445

Gln Ala
    450

<210> SEQ ID NO 20
<211> LENGTH: 527
<212> TYPE: PRT
<213> ORGANISM: Homo sapiens

<400> SEQUENCE: 20

Met Glu Asn Gln Glu Lys Ala Ser Ile Ala Gly His Met Phe Asp Val
1               5                   10                  15

Val Val Ile Gly Gly Gly Ile Ser Gly Leu Ser Ala Ala Lys Leu Leu
            20                  25                  30

Thr Glu Tyr Gly Val Ser Val Leu Val Leu Glu Ala Arg Asp Arg Val
        35                  40                  45

Gly Gly Arg Thr Tyr Thr Ile Arg Asn Glu His Val Asp Tyr Val Asp
    50                  55                  60

Val Gly Gly Ala Tyr Val Gly Pro Thr Gln Asn Arg Ile Leu Arg Leu

```
                65                  70                  75                  80
Ser Lys Glu Leu Gly Ile Glu Thr Tyr Lys Val Asn Val Ser Glu Arg
                        85                  90                  95
Leu Val Gln Tyr Val Lys Gly Lys Thr Tyr Pro Phe Arg Gly Ala Phe
                       100                 105                 110
Pro Pro Val Trp Asn Pro Ile Ala Tyr Leu Asp Tyr Asn Asn Leu Trp
                       115                 120                 125
Arg Thr Ile Asp Asn Met Gly Lys Glu Ile Pro Thr Asp Ala Pro Trp
            130                 135                 140
Glu Ala Gln His Ala Asp Lys Trp Asp Lys Met Thr Met Lys Glu Leu
145                 150                 155                 160
Ile Asp Lys Ile Cys Trp Thr Lys Thr Ala Arg Arg Phe Ala Tyr Leu
                    165                 170                 175
Phe Val Asn Ile Asn Val Thr Ser Glu Pro His Glu Val Ser Ala Leu
                180                 185                 190
Trp Phe Leu Trp Tyr Val Lys Gln Cys Gly Gly Thr Thr Arg Ile Phe
            195                 200                 205
Ser Val Thr Asn Gly Gly Gln Glu Arg Lys Phe Val Gly Gly Ser Gly
    210                 215                 220
Gln Val Ser Glu Arg Ile Met Asp Leu Leu Gly Asp Gln Val Lys Leu
225                 230                 235                 240
Asn His Pro Val Thr His Val Asp Gln Ser Ser Asp Asn Ile Ile Ile
                    245                 250                 255
Glu Thr Leu Asn His Glu His Tyr Glu Cys Lys Tyr Val Ile Asn Ala
                260                 265                 270
Ile Pro Pro Thr Leu Thr Ala Lys Ile His Phe Arg Pro Glu Leu Pro
            275                 280                 285
Ala Glu Arg Asn Gln Leu Ile Gln Arg Leu Pro Met Gly Ala Val Ile
        290                 295                 300
Lys Cys Met Met Tyr Tyr Lys Glu Ala Phe Trp Lys Lys Lys Asp Tyr
305                 310                 315                 320
Cys Gly Cys Met Ile Ile Glu Asp Glu Asp Ala Pro Ile Ser Ile Thr
                325                 330                 335
Leu Asp Asp Thr Lys Pro Asp Gly Ser Leu Pro Ala Ile Met Gly Phe
            340                 345                 350
Ile Leu Ala Arg Lys Ala Asp Arg Leu Ala Lys Leu His Lys Glu Ile
        355                 360                 365
Arg Lys Lys Lys Ile Cys Glu Leu Tyr Ala Lys Val Leu Gly Ser Gln
370                 375                 380
Glu Ala Leu His Pro Val His Tyr Glu Glu Lys Asn Trp Cys Glu Glu
385                 390                 395                 400
Gln Tyr Ser Gly Gly Cys Tyr Thr Ala Tyr Phe Pro Pro Gly Ile Met
                405                 410                 415
Thr Gln Tyr Gly Arg Val Ile Arg Gln Pro Val Gly Arg Ile Phe Phe
            420                 425                 430
Ala Gly Thr Glu Thr Ala Thr Lys Trp Ser Gly Tyr Met Glu Gly Ala
        435                 440                 445
Val Glu Ala Gly Glu Arg Ala Ala Arg Glu Val Leu Asn Gly Leu Gly
    450                 455                 460
Lys Val Thr Glu Lys Asp Ile Trp Val Gln Glu Pro Glu Ser Lys Asp
465                 470                 475                 480
Val Pro Ala Val Glu Ile Thr His Thr Phe Trp Glu Arg Asn Leu Pro
                485                 490                 495
```

-continued

Ser Val Ser Gly Leu Leu Lys Ile Ile Gly Phe Ser Thr Ser Val Thr
              500                 505                 510

Ala Leu Gly Phe Val Leu Tyr Lys Tyr Lys Leu Leu Pro Arg Ser
              515                 520                 525

<210> SEQ ID NO 21
<211> LENGTH: 520
<212> TYPE: PRT
<213> ORGANISM: Homo sapiens

<400> SEQUENCE: 21

Met Ser Asn Lys Cys Asp Val Val Gly Gly Gly Ile Ser Gly
1               5                   10                  15

Met Ala Ala Lys Leu Leu His Asp Ser Gly Leu Asn Val Val
                20                  25                  30

Leu Glu Ala Arg Asp Arg Val Gly Arg Thr Tyr Thr Leu Arg Asn
                35                  40                  45

Gln Lys Val Lys Tyr Val Asp Leu Gly Gly Ser Tyr Val Gly Pro Thr
    50                  55                  60

Gln Asn Arg Ile Leu Arg Leu Ala Lys Glu Leu Gly Leu Glu Thr Tyr
65                  70                  75                  80

Lys Val Asn Glu Val Glu Arg Leu Ile His His Val Lys Gly Lys Ser
                85                  90                  95

Tyr Pro Phe Arg Gly Pro Phe Pro Pro Val Trp Asn Pro Ile Thr Tyr
                100                 105                 110

Leu Asp His Asn Asn Phe Trp Arg Thr Met Asp Met Gly Arg Glu
                115                 120                 125

Ile Pro Ser Asp Ala Pro Trp Lys Ala Pro Leu Ala Glu Glu Trp Asp
                130                 135                 140

Asn Met Thr Met Lys Glu Leu Leu Asp Lys Leu Cys Trp Thr Glu Ser
145                 150                 155                 160

Ala Lys Gln Leu Ala Thr Leu Phe Val Asn Leu Cys Val Thr Ala Glu
                165                 170                 175

Thr His Glu Val Ser Ala Leu Trp Phe Leu Trp Tyr Val Lys Gln Cys
                180                 185                 190

Gly Gly Thr Thr Arg Ile Ile Ser Thr Thr Asn Gly Gly Gln Glu Arg
                195                 200                 205

Lys Phe Val Gly Gly Ser Gly Gln Val Ser Glu Arg Ile Met Asp Leu
                210                 215                 220

Leu Gly Asp Arg Val Lys Leu Glu Arg Pro Val Ile Tyr Ile Asp Gln
225                 230                 235                 240

Thr Arg Glu Asn Val Leu Val Glu Thr Leu Asn His Glu Met Tyr Glu
                245                 250                 255

Ala Lys Tyr Val Ile Ser Ala Ile Pro Pro Thr Leu Gly Met Lys Ile
                260                 265                 270

His Phe Asn Pro Pro Leu Pro Met Met Arg Asn Gln Met Ile Thr Arg
                275                 280                 285

Val Pro Leu Gly Ser Val Ile Lys Cys Ile Val Tyr Tyr Lys Glu Pro
                290                 295                 300

Phe Trp Arg Lys Lys Asp Tyr Cys Gly Thr Met Ile Ile Asp Gly Glu
305                 310                 315                 320

Glu Ala Pro Val Ala Tyr Thr Leu Asp Asp Thr Lys Pro Glu Gly Asn
                325                 330                 335

Tyr Ala Ala Ile Met Gly Phe Ile Leu Ala His Lys Ala Arg Lys Leu

|  |  |  |  | 340 |  |  |  | 345 |  |  |  | 350 |  |  |
|---|---|---|---|---|---|---|---|---|---|---|---|---|---|---|
| Ala | Arg | Leu | Thr | Lys | Glu | Glu | Arg | Leu | Lys | Lys | Leu | Cys | Glu | Leu | Tyr |
|  |  | 355 |  |  |  |  | 360 |  |  |  |  | 365 |  |  |  |
| Ala | Lys | Val | Leu | Gly | Ser | Leu | Glu | Ala | Leu | Glu | Pro | Val | His | Tyr | Glu |
|  | 370 |  |  |  |  | 375 |  |  |  |  | 380 |  |  |  |  |
| Glu | Lys | Asn | Trp | Cys | Glu | Glu | Gln | Tyr | Ser | Gly | Gly | Cys | Tyr | Thr | Thr |
| 385 |  |  |  |  | 390 |  |  |  |  | 395 |  |  |  |  | 400 |
| Tyr | Phe | Pro | Pro | Gly | Ile | Leu | Thr | Gln | Tyr | Gly | Arg | Val | Leu | Arg | Gln |
|  |  |  |  | 405 |  |  |  |  | 410 |  |  |  |  | 415 |  |
| Pro | Val | Asp | Arg | Ile | Tyr | Phe | Ala | Gly | Thr | Glu | Thr | Ala | Thr | His | Trp |
|  |  |  | 420 |  |  |  |  | 425 |  |  |  |  | 430 |  |  |
| Ser | Gly | Tyr | Met | Glu | Gly | Ala | Val | Glu | Ala | Gly | Glu | Arg | Ala | Ala | Arg |
|  |  |  | 435 |  |  |  | 440 |  |  |  |  | 445 |  |  |  |
| Glu | Ile | Leu | His | Ala | Met | Gly | Lys | Ile | Pro | Glu | Asp | Glu | Ile | Trp | Gln |
|  |  | 450 |  |  |  |  | 455 |  |  |  |  | 460 |  |  |  |
| Ser | Glu | Pro | Glu | Ser | Val | Asp | Val | Pro | Ala | Gln | Pro | Ile | Thr | Thr | Thr |
| 465 |  |  |  |  | 470 |  |  |  |  | 475 |  |  |  |  | 480 |
| Phe | Leu | Glu | Arg | His | Leu | Pro | Ser | Val | Pro | Gly | Leu | Leu | Arg | Leu | Ile |
|  |  |  |  | 485 |  |  |  |  | 490 |  |  |  |  | 495 |  |
| Gly | Leu | Thr | Thr | Ile | Phe | Ser | Ala | Thr | Ala | Leu | Gly | Phe | Leu | Ala | His |
|  |  |  | 500 |  |  |  |  | 505 |  |  |  |  | 510 |  |  |
| Lys | Arg | Gly | Leu | Leu | Val | Arg | Val |  |  |  |  |  |  |  |  |
|  |  | 515 |  |  |  |  | 520 |  |  |  |  |  |  |  |  |